US011229498B2

(12) United States Patent
Kamikawa et al.

(10) Patent No.: US 11,229,498 B2
(45) Date of Patent: Jan. 25, 2022

(54) MEDICAL SUPPORT ARM APPARATUS, MEDICAL SYSTEM, AND SURGICAL MICROSCOPE SYSTEM

(71) Applicant: SONY CORPORATION, Tokyo (JP)

(72) Inventors: Yasuhisa Kamikawa, Tokyo (JP); Yohei Kuroda, Tokyo (JP); Yasuhiro Matsuda, Tokyo (JP); Jun Arai, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 502 days.

(21) Appl. No.: 16/330,550

(22) PCT Filed: Aug. 3, 2017

(86) PCT No.: PCT/JP2017/028192
§ 371 (c)(1),
(2) Date: Mar. 5, 2019

(87) PCT Pub. No.: WO2018/051665
PCT Pub. Date: Mar. 22, 2018

(65) Prior Publication Data
US 2019/0328480 A1    Oct. 31, 2019

(30) Foreign Application Priority Data

Sep. 13, 2016  (JP) .............................. JP2016-178868

(51) Int. Cl.
*G05B 19/04*     (2006.01)
*A61B 90/25*     (2016.01)
(Continued)

(52) U.S. Cl.
CPC .............. *A61B 90/25* (2016.02); *A61B 90/50* (2016.02); *B25J 15/0019* (2013.01); *B25J 19/0016* (2013.01)

(58) Field of Classification Search
CPC .... B25J 15/0019; B25J 19/0016; B25J 13/08; B25J 19/00; A61B 2090/066;
(Continued)

(56) References Cited

U.S. PATENT DOCUMENTS

2011/0234977 A1  9/2011  Verdooner
2015/0250547 A1  9/2015  Fukushima et al.

FOREIGN PATENT DOCUMENTS

FR    3030337 A1 *  6/2016  ............. F16M 11/24
JP    7-93010 A       4/1995
(Continued)

OTHER PUBLICATIONS

International Search Report dated Oct. 10, 2017 in PCT/JP2017/028192, citing documents AR-AU therein, 2 pages
(Continued)

*Primary Examiner* — Harry Y Oh
(74) *Attorney, Agent, or Firm* — Xsensus LLP

(57) ABSTRACT

[Object] To make it possible to perform gravity compensation with a more compact and lightweight configuration.
[Solution] There is provided a medical support arm apparatus including: an arm section including multiple joint sections, and configured such that a medical tool is provided on a front end; an actuator at least provided in a compensated joint section that is a target of gravity compensation among the joint sections, and including a torque sensor that detects a torque acting on the compensated joint section; and a gravity compensation mechanism that imparts to the compensated joint section a compensating torque in a direction that cancels out a load torque due to a self-weight of the arm section acting on the compensated joint section.

14 Claims, 8 Drawing Sheets

(51) Int. Cl.
*A61B 90/50* (2016.01)
*B25J 15/00* (2006.01)
*B25J 19/00* (2006.01)

(58) Field of Classification Search
CPC . A61B 2090/5025; A61B 34/30; A61B 90/25; A61B 90/50
See application file for complete search history.

(56) References Cited

FOREIGN PATENT DOCUMENTS

| JP | 2006-230691 A | | 9/2006 |
| JP | 2006-263832 | * | 10/2006 |
| JP | 2006-263832 A | | 10/2006 |
| JP | 2008-87143 A | | 4/2008 |
| JP | 2012-240191 A | | 12/2012 |
| KR | 101459325 B1 | * | 11/2014 |
| KR | 101480346 B1 | * | 1/2015 |
| WO | WO 2013/161006 A1 | | 10/2013 |
| WO | WO 2015/046081 A1 | | 4/2015 |
| WO | WO 2015/137040 A1 | | 9/2015 |
| WO | WO-2015137040 A1 | * | 9/2015 ............. A61B 34/30 |

OTHER PUBLICATIONS

Gen Endo et al., "A Weight Compensation Mechanism with a Non-Circular Pulley and a Spring: Application to a Parallel Four-bar Linkage Arm", Journal of the Robotics Society of Japan, The Robotics Society of Japan, vol. 28, No. 1, Jan. 2010, pp. 77-84 and cover page.

Extended European Search Report dated Aug. 21, 2019, issued in corresponding European Patent Application No. 17850571.5.

* cited by examiner

MEDICAL SUPPORT ARM APPARATUS, MEDICAL SYSTEM, AND SURGICAL MICROSCOPE SYSTEM

TECHNICAL FIELD

The present disclosure relates to a medical support arm apparatus, a medical system, and a surgical microscope system.

BACKGROUND ART

Recently, in the medical field, support arm apparatus are being used to support examinations and surgeries. For example, a system has been proposed in which an observation tool for observing a surgical site such as an endoscope or a microscope is supported by an arm section of a support arm apparatus, and a doctor carries out an examination or surgery while watching an image captured by the observation tool. Alternatively, another proposal has been made in which a treatment tool such as forceps or a retractor is provided on the front end of the arm section, and the support arm apparatus is made to support or perform operations with the treatment tool that have been performed manually in the past. Note that in the following description, an observation tool, treatment tool, and the like provided on the front end of the arm section of a support arm apparatus are collectively designated medical tools. Also, in the following description, a support arm apparatus in which an observation tool is provided on the front end of the arm section is also called an observation apparatus.

Generally, to control with high precision the position and attitude of a medical tool provided on the front end of an arm section, and also to improve operability for the user when moving the medical tool, many innovations for compensating the gravitational force due to the weight of the arm section itself (that is, innovations for canceling out the torque acting on each joint section due to the self-weight) are applied to the arm apparatus of the support arm apparatus. By compensating the gravitational force of the arm section, since the attitude of the arm section is maintained without being influenced by the gravitational force, highly precise positioning of the medical tool may be achieved. Also, by compensating the gravitational force of the arm section, since the user becomes able to operate the arm section as though it were weightless, operability for the user may be improved.

For example, as exemplified in Patent Literature 1, 2 and Non-Patent Literature 1, gravity compensation mechanisms that mechanically compensate the torque acting on the joint sections of an arm section due to self-weight are being developed. Specifically, Patent Literature 1 discloses a gravity compensation mechanism including a combination of a spring, a working gear, and a belt. Patent Literature 2 discloses a gravity compensation mechanism including a combination of a spring and multiple non-circular gears. Non-Patent Literature 1 discloses a gravity compensation mechanism including a combination of a spring and a non-circular pulley.

Also, as another technology for compensating the gravitational force of the arm section, a technology is known in which a counterweight is provided on the base end side of the arm section such that the arm section as a whole is balanced (that is, such that the weight of the arm section itself may be supported), and the support arm apparatus is configured as what is called a balance arm.

Alternatively, in a support arm apparatus, providing actuators in each joint section of the arm section and driving these actuators appropriately to cause the arm section to operate is known (for example, Patent Literature 3). In the case of a support arm apparatus having such a configuration, by causing an actuator provided in each joint section to operate to support the self-weight of the arm section, it becomes possible to compensate the gravitational force acting on the arm section.

CITATION LIST

Patent Literature

Patent Literature 1: JP 2012-240191A
Patent Literature 2: WO 2013/161006
Patent Literature 3: WO 2015/046081

Non-Patent Literature

Non-Patent Literature 1: Gen Endo et al., "A Weight Compensation Mechanism with a Non-Circular Pulley and a Spring: Application to a Parallel Four-bar Linkage Arm", Journal of the Robotics Society of Japan, The Robotics Society of Japan, January 2010, Vol. 28, No. 1, pp. 77-84

DISCLOSURE OF INVENTION

Technical Problem

Herein, with a mechanical gravity compensation mechanism as illustrated in Patent Literature 1, 2 and Non-Patent Literature 1, the gravitational force acting on the arm section is compensated by the restoring force of the spring, but the restoring force demanded of the spring to compensate the gravitational force changes depending on the attitude of the arm section. Consequently, with these mechanical gravity compensation mechanisms, the gravity compensation mechanism is configured such that the amount of stretch in the spring is adjusted appropriately depending on the attitude of the arm section, and the spring produces a suitable restoring force. Accordingly, the structure of the gravity compensation mechanism tends to be complicated, and there is a risk of reduced mass productivity from the perspectives of cost and reliability.

Also, in the case of configuring the support arm apparatus as a balance arm, providing a counterweight causes the apparatus to become bulkier and heavier. Consequently, a higher proportion of space in the operating room becomes occupied by the support arm apparatus, and the surgical work may be impeded. Also, because the weight of the apparatus as a whole becomes heavier, for example, in the case of configuring the support arm apparatus as what is called a hanging support arm apparatus in which the arm section hangs down from the ceiling, large-scale construction work becomes necessary, and there are concerns regarding increased costs for installation.

Also, in the case of performing gravity compensation with an actuator provided in each joint section of the arm section, since a larger output becomes demanded of the actuators provided on the base end side of the arm section, the actuators on the base end side become bulkier. Consequently, the support arm apparatus itself also becomes bulkier and heavier, and there are concerns that inexpediences similar to the case of providing a counterweight may occur. Also, because a larger output is demanded of the actuators, there is also a risk of increased power consumption.

Accordingly, the present disclosure proposes a novel and improved medical support arm apparatus, medical system, and surgical microscope system capable of performing gravity compensation with a more compact and lightweight configuration.

Solution to Problem

According to the present disclosure, there is provided a medical support arm apparatus including: an arm section including multiple joint sections, and configured such that a medical tool is provided on a front end; an actuator at least provided in a compensated joint section that is a target of gravity compensation among the joint sections, and including a torque sensor that detects a torque acting on the compensated joint section; and a gravity compensation mechanism that imparts to the compensated joint section a compensating torque in a direction that cancels out a load torque due to a self-weight of the arm section acting on the compensated joint section.

In addition, according to the present disclosure, there is provided a medical system including: a medical support arm apparatus including an arm section including multiple joint sections, and configured such that an observation tool for observing a surgical site of a patient is provided on a front end, an actuator provided in at least one of the joint sections and including a torque sensor that detects a torque acting on the joint section, and a gravity compensation mechanism that imparts, to each joint section provided with the actuator, a compensating torque that compensates a load torque caused by a self-weight of the arm section acting on the joint section, and a control apparatus that causes the actuator to operate on the basis of at least a state of the joint section detected by the torque sensor, and controls a driving of the joint section; and a display apparatus that displays an image captured by the observation tool of the medical support arm apparatus.

In addition, according to the present disclosure, there is provided a surgical microscope system including: an arm section including multiple joint sections that include actuators; a microscope for imaging a surgical site of a patient, provided on a front end of the arm section such that an imaging direction is changeable by controlling the actuators; a gravity compensation mechanism that imparts to a compensated joint section, which is a target of gravity compensation among the joint sections, a compensating torque in a direction that cancels out a load torque due to a self-weight of the arm section acting on the compensated joint section; and a display apparatus that displays an image captured by the microscope.

According to the present disclosure, a compensating joint section, which is a target for performing gravity compensation from among multiple joint sections included in an arm section, is provided with an actuator including a torque sensor that detects a torque acting on the compensating joint section, and a gravity compensation mechanism that exerts a compensating torque in a direction that cancels out a load torque caused by the self-weight of the arm section acting on the compensating joint section. Consequently, when driving the actuator on the basis of the torque acting on the compensating joint section detected by the torque sensor, gravity compensation can be performed by taking the compensating torque into account to cause the actuator to operate to generate a torque that works to cancel out the load torque.

In other words, gravity compensation is performed by the combined use of the gravity compensation mechanism and the actuator. Consequently, compared to the case of performing gravity compensation with only a mechanical gravity compensation mechanism, the gravity compensation mechanism may have a simple configuration, while in addition, compared to the case of performing gravity compensation with only an actuator, the actuator may be configured more compactly. Thus, it becomes possible to perform gravity compensation while also configuring the arm section and the support arm apparatus in a more compact and lightweight configuration.

Advantageous Effects of Invention

According to the present disclosure as described above, it becomes possible to perform gravity compensation with a more compact and lightweight configuration. Note that the effects described above are not necessarily limitative. With or in the place of the above effects, there may be achieved any one of the effects described in this specification or other effects that may be grasped from this specification.

MODE(S) FOR CARRYING OUT THE INVENTION

Figure 1:
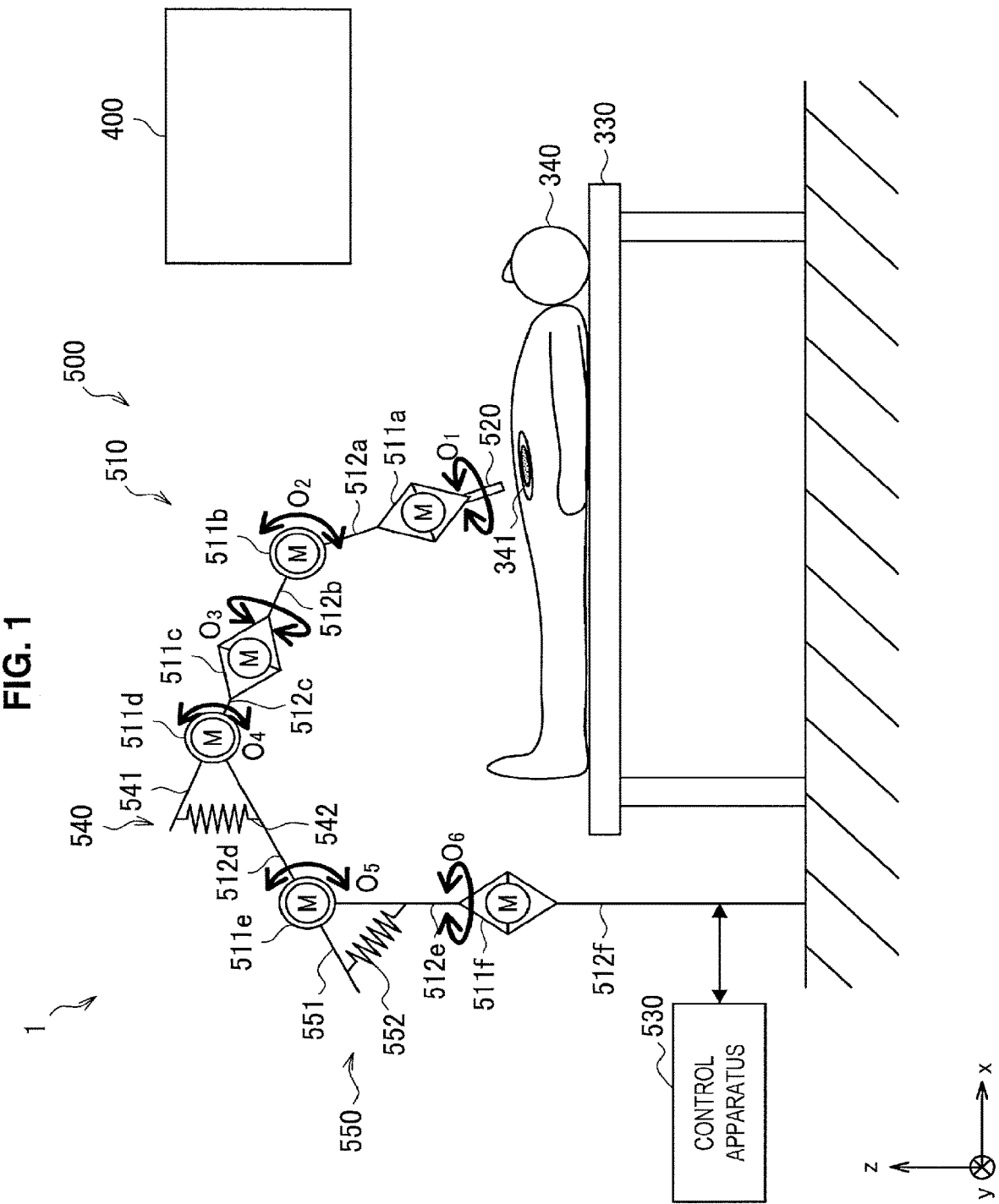
FIG. 1 is a diagram illustrating a schematic configuration of a system and a support arm apparatus according to the present embodiment.

Hereinafter, (a) preferred embodiment(s) of the present disclosure will be described in detail with reference to the appended drawings. Note that, in this specification and the appended drawings, structural elements that have substantially the same function and structure are denoted with the same reference numerals, and repeated explanation of these structural elements is omitted.

Hereinafter, the description will proceed in the following order.

1. Configuration of system and support arm apparatus
2. Functional configuration of system and support arm apparatus 2-1. Overview of control of operation of arm section
　　2-1-1. Generalized inverse dynamics
　　　　2-1-1-1. Virtual force computation process
　　　　2-1-1-2. Actual force computation process
　　2-1-2. Ideal joint control
2-2. Functional configuration
3. Example design of spring in gravity compensation mechanism
4. Control method of support arm apparatus
5. Modifications
5-1. Modification related to other control method
5-2. Modification related to hanging support arm apparatus
5-3. Other modifications
6. Comparison with typical gravity compensation
7. Supplement Note that in the following, the user who performs various operations with respect to the system and/or the support arm apparatus according to an embodiment of the present disclosure is designated the surgeon for the sake of convenience. However, this designation does not limit the user who uses the system and/or support arm apparatus, and various operations with respect to the system and/or the support arm apparatus may also be executed by any user, such as another member of the medical staff.

1. CONFIGURATION OF SYSTEM AND SUPPORT ARM APPARATUS

A configuration of a system and a support arm apparatus according to the present embodiment will be described with reference to FIG. 1. FIG. 1 is a diagram illustrating a schematic configuration of a system and a support arm apparatus according to the present embodiment.

FIG. 1 illustrates a situation in which a system 1 according to the present embodiment is used to perform abdominal surgery on a patient 340 on top of an operating table 330. Referring to FIG. 1, the system 1 includes a support arm apparatus 500 and a display apparatus 400. In the present embodiment, the support arm apparatus 500 is configured as an observation arm section 500 having a microscope section 520 provided on the front end of an arm section 510. The microscope section 520 is an electronic imaging microscope section 520 that electronically images a surgical site 341 of the patient 340 treated as the observation target. The image of the surgical site 341 captured by the microscope section 520 is displayed on the display apparatus 400 installed at a position visible to the surgeon, such as on a wall of the operating room, for example. The surgeon performs various treatments on the surgical site 341 while observing the surgical site 341 through the image appearing on the display apparatus 400.

(Support Arm Apparatus)

Referring to FIG. 1, the support arm apparatus 500 according to the present embodiment includes an arm section 510, a microscope section 520 that is attached to the front end of the arm section 510 and that is for performing enlarged observation of the surgical site 341 of the patient 340 treated as the observation target, and a control apparatus 530 that controls the operation of the support arm apparatus 500. Note that in FIG. 1, for the sake of simplicity, the support arm apparatus 500 is illustrated in a simplified manner. For example, in actuality, on the base end side of the arm section 510, a base section that supports the arm section 510 may be provided. Besides the above, the support arm apparatus 500 may also include various configurations that may be included in a typical support arm apparatus, to the extent that the configurations do not conflict with the description below.

(Microscope Section)

Although the illustration is simplified in FIG. 1, the microscope section 520 may have a configuration similar to a typical electronic imaging microscope section. Specifically, for example, the microscope section 520 includes an approximately cylindrical barrel section and an imaging section provided inside the barrel section.

On the bottom end of the barrel section, there is provided an aperture over which a cover glass is disposed. Light (hereinafter also called observation light) from the surgical site 341 treated as the observation target passes through the cover glass and is incident on the imaging section inside the barrel section. Note that a light source including a light-emitting diode (LED) or the like, for example, may also be provided inside the barrel section, and during imaging, light may be radiated from the light source onto the surgical site 341 through the cover glass.

The imaging section includes an optical system that condenses observation light, and an image sensor that receives the observation light condensed by the optical system. The optical system includes a combination of multiple lenses, including a zoom lens and a focus lens, the optical properties of which are adjusted such that an image of the observation light is formed on the light-sensitive face of the image sensor. The image sensor receives and photoelectrically converts the observation light to thereby generate a signal corresponding to the observation light, or in other words, an image signal corresponding to the observed image. The image sensor may be any of various known types of image sensors, such as a complementary metal-oxide-semiconductor (CMOS) image sensor or a charge-coupled device (CCD) image sensor. The image signal generated by the image sensor is transmitted to the control apparatus 530 as RAW data.

Also, the imaging section may include a driving mechanism that moves the zoom lens and the focus lens of the optical system along the optical axis. By suitably moving the zoom lens and the focus lens with the driving mechanism, the magnification of the captured image and the focal length during imaging may be adjusted. The adjustment of the magnification and focus in the microscope section 520 may be executed manually by the surgeon through an input apparatus (not illustrated) provided on the support arm apparatus 500, or may be executed automatically by using an autofocus (AF) function, for example. Additionally, any of various types of functions typically provided in electronic imaging microscope sections, such as an auto-exposure (AE) function and an electronic zoom function, may be provided in the imaging section.

In addition, the imaging section may be configured as what is called a one-chip imaging section that includes a single image sensor, or as what is called a multi-chip imaging section that includes multiple image sensors. In the case of configuring the imaging section in a multi-chip configuration, for example, the imaging section may include a pair of image sensors for respectively acquiring image signals for the right eye and the left eye corresponding to stereoscopic vision (3D display). By presenting a 3D display, the surgeon becomes able to grasp the depth of biological tissue in the surgical site 341 more accurately. Note that in the case of configuring the imaging section in a multi-chip configuration, the optical system may also be provided with multiple subsystems corresponding to each of the image sensors.

(Arm Section)

As described above, the base end section of the arm section 510 is attached to a base section (not illustrated) installed on the floor of the operating room, and is configured to extend from the base section. Note that in this specification, when describing the configuration of the arm section 510, the side on which the microscope section 520 is provided may also be called the front end side, the front end section, or the like, while the side near the floor may also be called the base end side, the base end section, or the like. Additionally, the vertical direction is also called the z-axis direction, while the two directions mutually orthogonal to the z-axis direction (that is, the two directions mutually orthogonal in the horizontal plane) are also called the x-axis direction and the y-axis direction, respectively.

The arm section 510 includes joint sections 511a, 511b, 511c, 511d, 511e, and 511f respectively provided at positions corresponding to each rotation axis (called the first axis $O_1$, the second axis $O_2$, the third axis $O_2$, the fourth axis $O_4$, the fifth axis $O_5$, and the sixth axis $O_6$ in order from the front end side), and multiple links 512a, 512b, 512c, 512d, 512e, and 512f rotatably joined to each other by the joint sections 511b to 511f.

Specifically, the base end of the link 512f that extends in an approximately vertical direction is attached to the base section. The front end of the link 512f is joined to the base end of the link 512e through the joint section 511f, and the link 512f rotatably supports the link 512e through the joint section 511f.

Thereafter, similarly, the front ends of the links 512e, 512d, 512c, and 512b are joined to the base ends of the links 512d, 512c, 512b and 512a through the joint sections 511e, 511d, 511c, and 511b, respectively. In addition, the links 512e, 512d, 512c, and 512b rotatably support the links 512d, 512c, 512b, and 512a through the joint sections 511e, 511d, 511c, and 511b, respectively.

The microscope section 520 is joined to the front end of the link 512a through the joint section 511a. The link 512a rotatably supports the microscope section 520 through the joint section 511a.

In this way, the base end of the link 512f connected to the base section acts as a fulcrum, and the ends of the multiple links 512a to 512f are joined to each other by the joint sections 511b to 511f, thereby forming an arm shape extending from the base section.

Note that although illustrated simply by solid lines in FIG. 1, in actuality, the links 512a to 512f may be rod-shaped or tube-shaped members having a predetermined thickness. Also, the cross-sectional shapes of the links 512a to 512f are not limited, and may be any of various types of shapes, such as circular, elliptical, or rectangular. As a specific structure of the links 512a to 512f, any of various types used as the links of a typical support arm apparatus may be applied.

Also, although illustrated simply by combinations of circles and triangles in FIG. 1, in actuality, the joint sections 511a to 511f have shafts that act as rotation axes, bearings that pivotally support the shafts, and the like, and may be members enabling the rotation of one member about another member. As a specific structure of the joint sections 511a to 511f, any of various types used as the joint sections of a typical support arm apparatus may be applied.

Among the rotation axes, the first axis $O_1$, the third axis $O_2$, and the sixth axis $O_6$ are rotation axes in a direction approximately parallel to the extension direction of the links 512a, 512c, and 512f provided on the base end side. In this specification, the rotation axes having such a direction are also called the yaw axes for convenience. On the other hand, the second axis $O_2$, the fourth axis $O_4$, and the fifth axis $O_5$ are rotation axes in a direction approximately orthogonal to the extension direction of the links 512b, 512d, and 512e provided on the base end side. In this specification, the rotation axes having such a direction are also called the pitch axes for convenience.

In other words, the arm section 510 is an arrangement of, from the base end side, a yaw axis (the sixth axis $O_6$), a pitch axis (the fifth axis $O_5$), a pitch axis (the fourth axis $O_4$), a yaw axis (the third axis $O_3$), a pitch axis (the second axis $O_2$), and a yaw axis (the first axis $O_1$), in that order. With this configuration, in the arm section 510, three degrees of translational freedom and three degrees of rotational freedom, for a total of six degrees of freedom, are realized with respect to the motion of the microscope section 520. By configuring the arm section 510 to have six degrees of freedom, it becomes possible to move the microscope section 520 freely inside the movable range of the arm section 510.

However, the configuration of the arm section 510 is not limited to the illustrated example. In the present embodiment, it is sufficient for the arm section 510 to be configured to have the necessary degrees of freedom to execute a desired purpose of motion (task), and the numbers and arrangement of the joint sections 511a to 511f and the links 512a to 512f, the directions of the drive axes of the joint sections 511a to 511f, the lengths of the links 512a to 512f, and the like may be set appropriately such that the arm section 510 has the desired degrees of freedom. However, as described above, by configuring the arm section 510 to have six degrees of freedom, it becomes possible to move the microscope section 520 freely, and therefore the arm section 510 preferably is configured to have degrees of freedom equal to or greater than six degrees of freedom.

Figure 2:
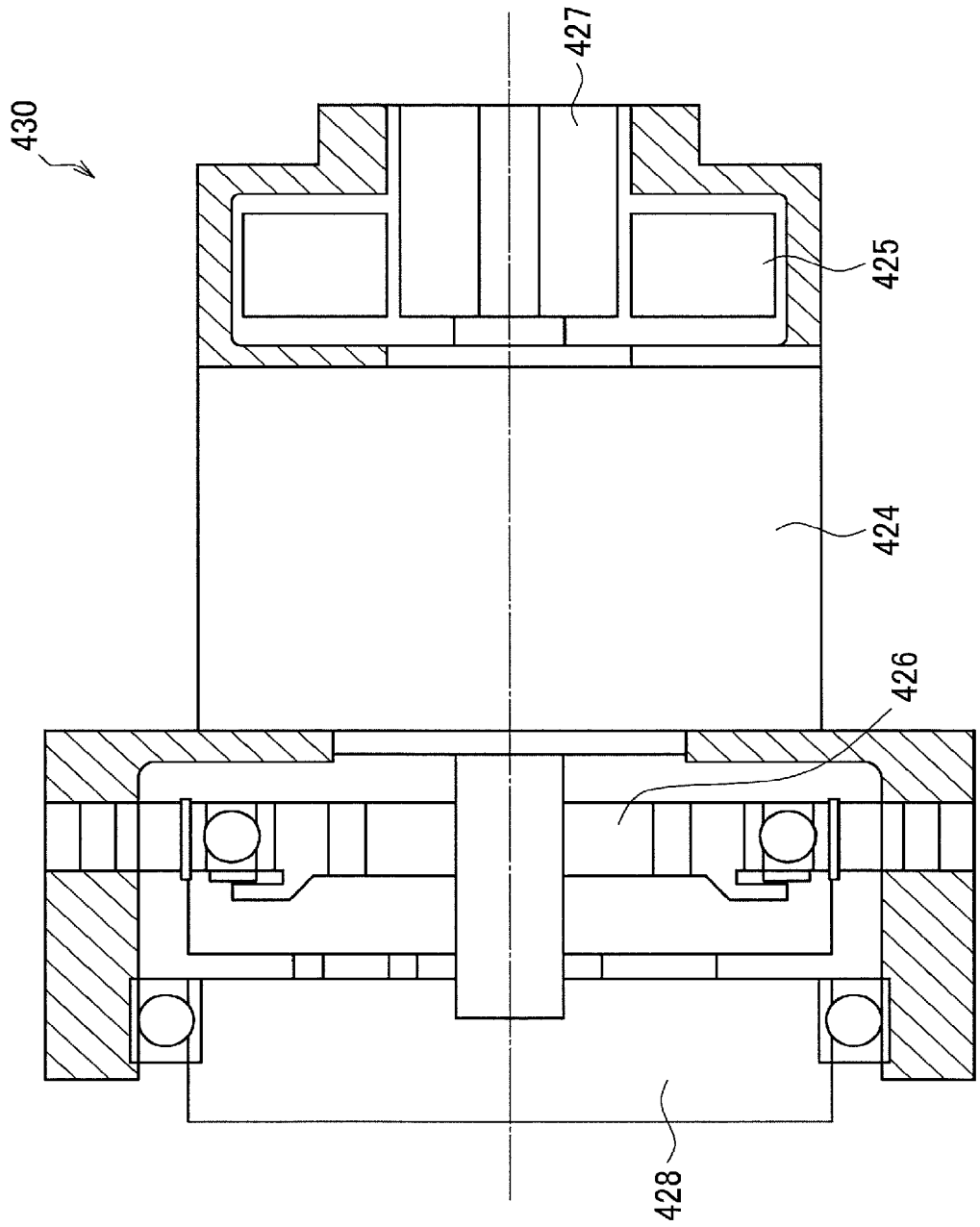
FIG. 2 is a cross-section diagram illustrating an exemplary configuration of an actuator provided in a joint section of the support arm apparatus illustrated in FIG. 1.

The joint sections 511a to 511f are provided with an actuator 430 illustrated in FIG. 2. The joint sections 511a to 511f are rotationally driven about a predetermined rotation axis by the actuator 430. The driving of the actuator 430 is controlled by the control apparatus 530. By controlling the driving of each actuator 430 in each of the joint sections 511a to 511f, the driving of the arm section 510 is controlled to extend or contract (fold up) the arm section 510, for example.

FIG. 2 will be referenced to describe the configuration of the actuator 430 in detail. FIG. 2 is a cross-section diagram illustrating an exemplary configuration of the actuator 430 provided in the joint sections 511a to 511f of the support arm apparatus 500 illustrated in FIG. 1. FIG. 2 illustrates a cross-section view of the actuator 430 according to the present embodiment in the case of cutting on a plane that goes through the rotation axis.

Referring to FIG. 2, the actuator 430 according to the present embodiment includes a motor 424, a motor driver 425, a reduction gear 426, an encoder 427, and a torque sensor 428. The actuator 430 is an actuator corresponding to force control, for example. In the actuator 430, the rotation of the motor 424 is reduced by the reduction gear 426 at a predetermined reduction ratio, and transmitted to other downstream members via an output shaft. As a result, the other members are driven.

The motor 424 is a driving mechanism that produces rotational driving force. The motor 424, under control from the motor driver 425, is driven to generate torque corresponding to a torque command value $\tau$ illustrated in FIG. 3 described later. For the motor 424, a brushless motor is used, for example. However, the present embodiment is not limited to such an example, and any of various known types of motors may be used as the motor 424.

The motor driver 425 is a driver circuit (driver integrated circuit (IC)) that rotationally drives the motor 424 by supplying current to the motor 424, and is able to control the rotation rate of the motor 424 by adjusting the amount of current supplied to the motor 424. The motor driver 425 drives the motor 424 by supplying the motor 424 with a current corresponding to the torque command value $\tau$ illustrated in FIG. 3 described later.

Additionally, the motor driver 425 is able to adjust a viscous drag coefficient on rotary motion of the actuator 430 by adjusting the amount of current supplied to the motor 424. With this arrangement, it becomes possible to impose a predetermined drag on rotary motion in the actuator 430, or in other words, on rotary motion in the joint sections 511a to 511f. For example, the joint sections 511a to 511f can be put into a state of easily rotating in response to a force imparted from the outside (in other words, a state in which the arm section 510 is easy to move by hand), or conversely, can be put into a state of hardly rotating in response to a force imparted from the outside (in other words, a state in which the arm section 510 is hard to move by hand).

The reduction gear 426 is joined to the rotating shaft (drive shaft) of the motor 424. The reduction gear 426 reduces by a predetermined reduction ratio the rotational velocity of the rotating shaft of the joined motor 424 (in other words, the rotational velocity of the input shaft), and transmits to the output shaft. In the present embodiment, the configuration of the reduction gear 426 is not limited to a specific configuration, and any of various known types of reduction gears may be used as the reduction gear 426. However, for the reduction gear 426, it is preferable to use one capable of setting the reduction ratio with high precision, such as a Harmonic Drive (registered trademark), for example. In addition, the reduction ratio of the reduction gear 426 may be set appropriately according to the application of the actuator 430. For example, in the case of applying the actuator 430 to the joint sections 511a to 511f of the support arm apparatus 500 as in the present embodiment, a reduction gear 426 having a reduction ratio of approximately 1:100 may be used favorably.

The encoder 427 detects the rotational angle of the input shaft (that is, the rotational angle of the rotating shaft of the motor 424). On the basis of the rotation rate of the input shaft detected by the encoder 427, and the reduction ratio of the reduction gear 426, information such as the rotational angle, the rotational angular velocity, and the rotational angular acceleration of the joint sections 511a to 511f may be obtained. For the encoder 427, any of various known types of rotary encoders, such as a magnetic encoder or an optical encoder, for example, may be used. Note that in the illustrated example, the encoder 427 is provided only on the input shaft of the actuator 430, but an encoder for detecting the rotational angle and the like of the output shaft of the actuator 430 additionally may be provided farther downstream than the reduction gear 426.

The torque sensor 428 is connected to the output shaft of the actuator 430, and detects the torque acting on the actuator 430. The torque sensor 428 detects the torque output by the actuator 430 (generated torque). Additionally, the torque sensor 428 is also able to detect external torque imparted to the actuator 430 from the outside.

The above references FIG. 2 to describe a configuration of the actuator 430 according to the present embodiment. Herein, in the present embodiment, the behavior of the arm section 510 is controlled by force control. With such force control, in the support arm apparatus 500, the rotational angle of each of the joint sections 511a to 511f and the torque acting on each of the joint sections 511a to 511f are detected respectively by the encoder 427 and the torque sensor 428 provided in each actuator 430. At this time, the torque acting on each of the joint sections 511a to 511f detected by the torque sensor 428 may also include force acting on the arm section 510 and/or the microscope section 520.

Although described later, on the basis of the rotational angles detected by the encoders 427 and the torque values detected by the torque sensors 428, the current state of the arm section 510 (such as the position and velocity) may be acquired. In the support arm apparatus 500, on the basis of the acquired state of the arm section 510 (arm state), the torque that needs to be generated by the actuator 430 in each of the joint sections 511a to 511f in order for the arm section 510 to execute a desired task is computed, and this torque is used as a control value to drive the actuator 430 in each of the joint sections 511a to 511f.

Note that the configuration illustrated in FIG. 2 merely illustrates one exemplary configuration of the actuator 430, and the present embodiment is not limited to such an example. For the actuator 430, it is possible to use any of various known types of actuators typically used in various devices whose behavior is controlled by force control. For example, the configurations described in previous patents by the applicant, such as JP 2009-269102A and JP 2011-209099A, may also used favorably as the actuator 430.

Furthermore, in the present embodiment, gravity compensation mechanisms 540 and 550 are provided in the joint section 511d corresponding to the fourth axis $O_4$ and the joint section 511e corresponding to the fifth axis $O_5$, respectively. The gravity compensation mechanism 540 imparts to the joint section 511d a torque in a direction that cancels out the load torque due to the self-weight of the arm section 510 acting on the joint section 511d. The gravity compensation mechanism 550 imparts to the joint section 511e a torque in a direction that cancels out the load torque due to the self-weight of the arm section 510 acting on the joint section 511e. In the following, a torque that is in a direction that cancels out the load torque and that is imparted by the gravity compensation mechanisms 540 and 550 for gravity compensation is also designated a compensating torque.

Specifically, as illustrated in the drawing, the gravity compensation mechanism 540 includes a hooking section 541 provided in a fixed manner (that is, rotating together with the link 512c about the joint section 511d) with respect to the link 512c connected to the front end side of the joint section 511d, and a spring 542 stretched in tension between the hooking section 541 and the link 512d connected to the base end side of the joint section 511d. According to such a configuration, in the case in which the configuration on the front end side from the link 512c rotates about the joint section 511d in the direction of gravity acting on the configuration on the front end side from the link 512c, the spring 542 is stretched in accordance with the rotation amount. At this time, the restoring force of the stretched spring 542 acts on the configuration on the front end side from the link 512c in a direction causing the configuration on the front end side from the link 512c to rotate in the reverse direction of the rotation in the direction of gravity about the joint section 511d. In other words, the restoring force of the spring 542 imparts to the joint section 511d a compensating torque in the direction that cancels out the load torque due to the self-weight of the configuration on the front end side from the link 512c acting on the joint section 511d.

Similarly, the gravity compensation mechanism 550 includes a hooking section 551 provided in a fixed manner (that is, rotating together with the link 512d about the joint section 511e) with respect to the link 512d connected to the front end side of the joint section 511e, and a spring 552 stretched in tension between the hooking section 551 and the link 512e connected to the base end side of the joint section 511e. According to such a configuration, in the case in which the configuration on the front end side from the link 512d rotates about the joint section 511e in the direction of gravity acting on the configuration on the front end side from the link 512d, the spring 552 is stretched in accordance with the rotation amount. At this time, the restoring force of the stretched spring 552 acts on the configuration on the front end side from the link 512d in a direction causing the configuration on the front end side from the link 512d to rotate in the reverse direction of the rotation in the direction of gravity about the joint section 511e. In other words, the restoring force of the spring 552 imparts to the joint section 511e a compensating torque in the direction that cancels out the load torque due to the self-weight of the configuration on the front end side from the link 512d acting on the joint section 511e.

The springs 542 and 552 are tension springs, for example. However, the present embodiment is not limited to such an example, and any of various types of known springs, such as compression springs and torsion coil springs, for example, may be used as the springs 542 and 552. Alternatively, instead of the springs 542 and 552, other elastic bodies that produce a restoring force in response to expansion or contraction may be used.

Herein, as described above, in the present embodiment, the gravity compensation mechanism 540 has a simple configuration including the hooking section 541 and the spring 542. By such a configuration, in the gravity compensation mechanism 540, the restoring force of the spring 542 has a simple positive correlation of increasing as the rotational angle in the joint section 511d increases, and decreasing as the rotational angle decreases. In other words, the restoring force of the spring 542 may vary monotonically with respect to the rotational angle in the joint section 511d.

In contrast, the load torque due to the self-weight of the arm section 510 acting on the joint section 511d is expressed by the product of the magnitude of the gravitational force acting on the configuration on the front end side from the joint section 511d and the length of the moment arm (in other words, the normal line extending from the center of rotation of the joint section 511d towards a vector indicating the direction of the gravitational force), but depending on the configuration of the arm section 510, the length of the moment arm does not necessarily vary monotonically with respect to the rotational angle in the joint section 511d, and therefore the magnitude of the load torque likewise does not necessarily vary monotonically with respect to the rotational angle. In addition, the compensating torque acting on the joint section 511d by the restoring force of the spring 542 is expressed by the product of the magnitude of the restoring force and the length of the moment arm (in other words, the normal line extending from the center of rotation of the joint section 511d towards a vector indicating the direction of the restoring force), but depending on the configuration of the arm section 510, the length of the moment arm also does not necessarily vary monotonically with respect to the rotational angle in the joint section 511d, and therefore the compensating torque likewise does not necessarily vary monotonically with respect to the rotational angle.

In this way, although the restoring force of the spring 542 of the gravity compensation mechanism 540 may vary monotonically with respect to the rotational angle in the joint section 511d, the load torque due to the self-weight of the arm section 510 acting on the joint section 511d and the compensating torque acting on the joint section 511d by the restoring force of the spring 542 may vary complexly with respect to the rotational angle in the joint section 511d. Consequently, in the gravity compensation mechanism 540 having a simple configuration like in the present embodiment, it is difficult to produce a compensating torque to nearly completely cancel out the load torque due to the self-weight of the arm section 510. The foregoing description takes the gravity compensation mechanism 540 as an example, but the situation is also similar for the gravity compensation mechanism 550.

Accordingly, in the present embodiment, the compensating torque imparted to the joint section 511d by the gravity compensation mechanism 540 is taken into account to execute gravity compensation by driving the actuator 430 provided in the joint section 511d such that the load torque due to the self-weight of the arm section 510 may be canceled out. In other words, gravity compensation is executed by imparting torque to the joint section 511d by the actuator 430 such that the insufficiency not fully compensated by the gravity compensation mechanism 540, which is obtained by subtracting the compensating torque imparted to the joint section 511d by the gravity compensation mechanism 540 from the load torque due to the self-weight of the arm section 510 acting on the joint section 511d, may be compensated. In this way, in the present embodiment, gravity compensation in the joint section 511d is executed by using both the gravity compensation mechanism 540 and the actuator 430 provided in the joint section 511d. Likewise for the joint section 511e, gravity compensation in the joint section 511e is executed by using both the gravity compensation mechanism 550 and the actuator 430 provided in the joint section 511e. Note that a method of controlling the driving of the actuators 430 during gravity compensation will be described in detail in (2-2. Functional configuration) below.

(Control Apparatus)

The control apparatus 530 includes a processor such as a central processing unit (CPU) or a digital signal processor (DSP), or a control board or the like on which these processors are mounted together with a storage element such as memory. The control apparatus 530 controls the operation of the support arm apparatus 500 by executing signal processing following a predetermined program.

The control apparatus 530 controls the operation of the arm section 510. In the present embodiment, force control is used as the control method of the arm section 510. With force control, the state of each of the joint sections 511a to 511f (the forces acting on the arm section 510 and the microscope section 520, the rotational angle in each of the joint sections 511a to 511f, and the like) is detected by the encoder 427 and the torque sensor 428 of the actuator 430 provided in each of the joint sections 511a to 511f. On the basis of the detected state of each joint sections 511a to 511f, the control apparatus 530 computes a generated torque that needs to be generated by the actuator 430 provided in each of the joint sections 511a to 511f to cause the arm section 510 to execute a desired task, and uses the computed generated torque as a control value to control the driving of the actuator 430 in each of the joint sections 511a to 511f. At this point, in the present embodiment, the control apparatus 530 computes the generated torque by taking into account the compensating torque by the gravity compensation mechanisms 540 and 550 as described above, and computes the generated torque to achieve execution of the desired task while also executing gravity compensation.

With force control, it becomes possible to control the driving of each of the joint sections 511a to 511f according to the external force on the arm section 510. For example, with force control, the driving of the actuators 430 and the operation of the arm section 510 may be controlled by the control apparatus 530 in response to an operation in which the surgeon touches the arm section 510 directly to move the arm section 510, for example, such that the arm section 510 moves in the direction of a force imparted to the arm section 510 (in other words, to track the operation of the surgeon). Such operation of the arm section 510 is an operation of assisting a manipulation by the surgeon, and thus is called a power assist operation. In this way, by using force control, the surgeon is able to move the arm section 510 while touching the arm section 510 directly, thereby making easier and more intuitive operations possible. Note that in the following description, an operation in which the surgeon moves the arm section 510 while touching the arm section 510 directly will also be called a direct operation.

Note that the functions related to the control of such operation of the arm section 510 in the control apparatus 530 will be described in further detail in (2. Functional configuration of system and support arm apparatus) below.

Also, the control apparatus 530 executes various processes related to display control for an image captured by the microscope section 520. Specifically, the control apparatus 530 performs various types of signal processing on an image signal acquired by the imaging section of the microscope section 520, and thereby generates image data for display. For the signal processing, any of various known types of signal processing, such as a development process (demosaicing process), an image quality-improving process (such as a band enhancement process, a super-resolution process, a noise reduction (NR) process, and/or a shake correction process), and/or an enlargement process (that is, an electronic zoom process), may be performed. The control apparatus 530 transmits the generated image data to the display apparatus 400 while also controlling the driving of the display apparatus 400 to cause the display apparatus 400 to display the image data.

Besides the above, the control apparatus 530 may also include any of various functions included in a typical observation apparatus 500.

(Display Apparatus)

The display apparatus 400 is installed inside the operating room, and under control from the control apparatus 530, displays an image corresponding to image data generated by the control apparatus 530. In other words, on the display apparatus 400, an image of the surgical site 341 captured by the microscope section 520 is displayed. Any of various known types of display apparatus, such as a liquid crystal display apparatus or an electroluminescence (EL) display apparatus, for example, may be applied as the display apparatus 400.

The above describes a configuration of the system 1 and the support arm apparatus 500 according to the present embodiment.

Herein, as described above, in the case of attempting to execute gravity compensation with only a mechanical gravity compensation mechanism like the technologies illustrated in Patent Literature 1, 2 and Non-Patent Literature 1, since it is necessary to consider the dependency of the length of the moment arm in the load torque due to the self-weight of the arm section and length of the moment arm in the compensating torque by the gravity compensation mechanism with respect to the rotational angle in the joint section to configure the gravity compensation mechanism to produce a compensating torque such that the load torque corresponding to the rotational angle may be canceled out, the configuration of the gravity compensation mechanism has had a tendency of becoming complicated. Additionally, in a support arm apparatus in which an actuator is provided in each joint section as illustrated in Patent Literature 3, in the case of attempting to execute gravity compensation with only the actuator, since a large output is demanded of the actuator, the actuator has had a tendency of becoming bulky. Such increased complexity in the configuration of the gravity compensation mechanism and increased bulk of the actuator causes increased bulk and weight of the arm section, and by extension, the support arm apparatus as a whole. Also, in a support arm apparatus configured as a balance arm, providing a counterweight unsurprisingly has a tendency of increasing the bulk and weight of the arm section and the support arm apparatus as a whole.

In contrast, as described above, according to the present embodiment, gravity compensation in the joint sections 511d and 511e is executed by using both the gravity compensation mechanisms 540 and 550 and the actuators 430 provided in the joint sections 511d and 511e. By additionally using the actuators 430, since it is not necessary to form the gravity compensation mechanisms 540 and 550 such that the load torque due to the self-weight of the arm section 510 may be canceled out nearly completely by the gravity compensation mechanisms 540 and 550 having a mechanical configuration, the configuration of the gravity compensation mechanisms 540 and 550 may be simplified. Also, by additionally using the gravity compensation mechanisms 540 and 550, since a relatively large output is not demanded of the actuators 430 during gravity compensation, the actuators 430 may be made more compact. Consequently, according to the present embodiment, it becomes possible to configure the arm section 510 and the support arm apparatus 500 as a whole in a simpler and more lightweight configuration.

In the present embodiment, by eliminating the need for actuators with large output, advantageous effects of reduced power consumption and reduced manufacturing costs may also be obtained. Also, by making it possible to configure the arm section 510 and the support arm apparatus 500 as a whole in a simpler and more lightweight configuration, configurations with a greater degree of freedom become possible, such as disposing the support arm apparatus 500 close to the operating table 330, or configuring the support arm apparatus 500 as a hanging support arm apparatus 500 in which the arm section 510 is configured to hang down from the ceiling.

In addition, the load torque due to the self-weight of the arm section 510 imparted to the joint sections 511d and 511e depends on the weights and the center-of-gravity positions of the configurations farther on the front end side than the joint sections 511d and 511e, and therefore is different for these joint sections 511d and 511e. Consequently, if one attempts to execute gravity compensation with only the generated torque from the actuators 430, for example, different performance will be demanded of the actuator 430 provided in the joint section 511d and the actuator 430 provided in the joint section 511e, and therefore the actuators 430 cannot be standardized, which may lead to increased manufacturing costs. In contrast, in the present embodiment, since the joint sections 511d and 511e are provided with the gravity compensation mechanisms 540 and 550, respectively, by adjusting the configurations of such gravity compensation mechanisms 540 and 550 (specifically, the restoring forces of the springs 542 and 552, and the like) and appropriately adjusting the compensating torque values to be generated by each of the gravity compensation mechanisms 540 and 550, it becomes possible to make the outputs demanded of the actuator 430 provided in the joint section 511*d* and the actuator 430 provided in the joint section 511*e* comparable with each other. In this way, according to the present embodiment, by appropriately adjusting the configurations of the gravity compensation mechanisms 540 and 550, standardization of the actuators 430 may be attained. Consequently, it is possible to contribute further to a reduction in manufacturing costs.

In addition, by making it possible to configure the gravity compensation mechanisms 540 and 550 with simpler configurations, the reliability of the gravity compensation mechanisms 540 and 550 can be improved while also keeping manufacturing costs down, thereby making it possible to provide a support arm apparatus 500 favorable for mass production.

Furthermore, in the present embodiment, gravity compensation is executed using the actuator 430 that includes the torque sensor 428. Since the torque actually acting on the actuator 430 can be detected by the torque sensor 428 and the generated torque of the actuator 430 for executing gravity compensation can be computed on the basis of the detected torque, it becomes possible to execute highly precise gravity compensation with a narrow dead zone.

2. FUNCTIONAL CONFIGURATION OF SYSTEM AND SUPPORT ARM APPARATUS

While describing the functional configuration of the system 1 and the support arm apparatus 500 described above, the control of the operations of the arm section 510 according to the present embodiment will be described.

(2-1. Overview of Control of Operation of Arm Section)

Before describing the functional configuration of the system 1 and the support arm apparatus 500 according to the present embodiment described above, an overview of processes performed to control the operations of the arm section 510 of the support arm apparatus 500 will be described. Note that each process for controlling the operations of the arm section 510 described below is merely one example. In the present embodiment, it is sufficient for the operations of the arm section 510 to be controlled by force control, and the specific control method is not limited. In the control of the operations of the arm section 510, any of various known control theories related to force control are preferably used.

In the present embodiment, the driving of each of the joint sections 511*a* to 511*f* of the support arm apparatus 500 is controlled by whole body cooperative control using generalized inverse dynamics. With whole body cooperative control, the torque to be generated in each of the joint sections 511*a* to 511*f* (that is, the generated torque in the actuator 430 of each of the joint sections 511*a* to 511*f* for executing a desired task) is computed as a control value of the actuator 430 provided in each of the joint sections 511*a* to 511*f*, such that the desired task may be executed under a predetermined constraint condition. Furthermore, ideal joint control that achieves an ideal response with respect to the control value by correcting the influence of disturbances is applied to the driving control of each of the joint sections 511*a* to 511*f*. Hereinafter, an overview of generalized inverse dynamics and ideal joint control will be described in order.

(2-1-1. Generalized Inverse Dynamics)

Generalized inverse dynamics is a basic computation for whole body cooperative control of a multi-link structure (in the present embodiment, the arm section 510) including multiple links joined to each other by joint sections, in which a task related to various dimensions in various types of operation spaces is converted into torques to be generated in the multiple joint sections, while also accounting for various constraint conditions.

An operation space is an important concept for force control of a multi-link structure. An operation space is a space for describing the relationship between the force acting on a multi-link structure and the acceleration of the multi-link structure. When controlling the driving of a multi-link structure by force control rather than position control, the concept of an operation space becomes necessary in the case of using the way in which the multi-link structure and the environment interact as a constraint condition. An operation space is a space to which the multi-link structure belongs, such as a joint space, a Cartesian space, a momentum space, or the like, for example.

A task is an expression of a target for driving control of the multi-link structure. As the task, for example, "maintain viewpoint of imaging section" (that is, keep the position and the attitude of the microscope section 520 constant), "secure field of view for surgeon" (that is, do not allow the arm section 510 and the microscope section 520 to intrude into the surgeon's field of view), and the like may be set. In actual control, more specifically, target values for the position, velocity, acceleration, force, impedance, and the like of the multi-link structure for achieving these tasks may be set.

The constraint condition is a constraint condition related to the position, velocity, acceleration, force, and the like of the multi-link structure, which are determined by the shape and structure of the multi-link structure, the environment surrounding the multi-link structure, settings set by the user, and the like. For example, the constraint condition includes information about the generated force, the priority, the presence or absence of non-driven joints, the vertical reaction force, friction weighting, a support polygon, and the like.

The constraint condition may be set according to the task. For example, if the task is to "maintain viewpoint of imaging section", geometric restrictions are imposed as a constraint condition on the front end position (fingertip position) and front end attitude (fingertip attitude) of the arm section 510, such that the fingertip position and the fingertip attitude are kept in a predetermined state. As another example, if the task is to "secure field of view for surgeon", restrictions are imposed as a constraint condition on the movement range such that the arm section 510 and the microscope section 520 do not intrude into a predetermined invasion prohibition region set in space. For the invasion prohibition region, a region anticipated to be the region of the surgeon's field of view is set appropriately.

In generalized dynamics, to achieve both stability in numerical calculations and computational efficiency enabling real-time processing, the computational algorithm includes a first stage of a virtual force decision process (virtual force computation process), and a second stage of an actual force conversion process (actual force computation process). In the first stage of the virtual force computation process, the virtual force, which is a virtual force acting on the operation space required to achieve a task, is decided while also accounting for the priority of the task and a maximum value of the virtual force. In the second stage of the actual force computation process, the virtual force obtained above is converted into actual force realizable with the configuration of the actual multi-link structure, such as joint force and external force, while also accounting for constraints related to non-driven joints, vertical reaction force, friction weighting, a support polygon, and the like. Hereinafter, the virtual force computation process and the actual force computation process will be described in detail.

(2-1-1-1. Virtual Force Computation Process)

Let a generalized variable q (also called the joint value q or the joint space q) be a vector including a certain physical quantity in each joint section of a multi-link structure. An operation space x is defined by Formula (1) below, using the generalized variable q and the Jacobian J.

[Math. 1]

$$\dot{x} = J\dot{q} \tag{1}$$

Given the configuration of the support arm apparatus 500 according to the present embodiment, for example, x in the above Formula (1) is the front end position of the links 512a to 512f of the arm section 510, while q is the rotational angle in the joint sections 511a to 511f of the arm section 510. An equation of motion related to the operation space x is stated by Formula (2) below.

[Math. 2]

$$\ddot{x} = \Lambda^{-1} f + c \tag{2}$$

Herein, f represents the force acting on the operation space x. Also, $\Lambda^{-1}$ is the inverse inertia matrix of the operation space, while c is called the bias acceleration of the operation space. These quantities are expressed in Formulas (3) and (4) below, respectively.

[Math. 3]

$$\Lambda^{-1} = JH^{-1}J^T \tag{3}$$

$$c = JH^{-1}(\tau - b) + \dot{J}\dot{q} \tag{4}$$

Note that H is the inertia matrix of the joint space, τ is the joint force corresponding to the joint value q (for example, the generated torque in the joint sections 511a to 511f), and b is a term representing the gravitational force, the Coriolis force, and the centrifugal force.

In generalized inverse dynamics, it is known that target values of the position and velocity related to the operation space x corresponding to a task can be expressed as the acceleration of the operation space x. At this point, from Formula (1) above, to realize an operation space acceleration which is a target value given in accordance with a task, the virtual force f, that needs to act on the operation space x is obtained by solving a type of linear complementary problem (LCP) like Formula (5) below.

[Math. 4]

$$w + \ddot{x} = \Lambda^{-1} f_v + c \tag{5}$$

$$\text{s.t.} \begin{cases} ((w_i < 0) \cap (f_{v_i} = U_i)) \cup \\ ((w_i > 0) \cap (f_{v_i} = L_i)) \cup \\ ((w_i = 0) \cap (L_i < f_{v_i} < U_i)) \end{cases}$$

Herein, $L_i$ and $U_i$ are taken to be the negative lower-bound value (including $-\infty$) of the ith component of $f_v$ and the positive upper-bound value (including $+\infty$) of the ith component of $f_v$, respectively. The above LCP can be solved using a method of applying the iterative method, the pivot method, robust acceleration control, or the like, for example.

Note that the inverse inertia matrix $\Lambda^{-1}$ of the operation space and the bias acceleration c are computationally expensive if computed according to the definitions of these terms in Formulas (3) and (4) above. Consequently, there is proposed a method of carrying out the process of computing the inverse inertia matrix $\Lambda^{-1}$ of the operation space more quickly by applying forward dynamics (FWD) computations, which obtain a generalized acceleration (joint acceleration) from the generalized force (joint force z) of the multi-link structure. Specifically, by using forward dynamics (FWD) computations, the inverse inertia matrix $\Lambda^{-1}$ of the operation space and the bias acceleration c can be obtained from information related to forces acting on the the multi-link structure, such as the joint space q, the joint force τ, and gravity g. In this way, by applying forward dynamics (FWD) computations related to the operation space, the inverse inertia matrix $\Lambda^{-1}$ of the operation space can be calculated with a computational complexity O(N) with respect to the number N of joint sections.

At this point, as an example setting of a target value corresponding to a task, a condition for achieving a target value of the operation space acceleration (indicated by the superscript bar over the second derivative of x) with a virtual force $f_{vi}$ that is less than or equal to the absolute value of $F_i$ can be expressed by Formula (6) below.

[Math. 5]

$$L_i = -F_i,$$

$$U_i = F_i,$$

$$\ddot{x}_i = \ddot{\bar{x}}_i \tag{6}$$

Also, as described above, the target value related to the position and velocity of the operation space x can be expressed as a target value of the operation space acceleration, specifically by Formula (7) below (the position and velocity of the operation space x are indicated by a superscript bar over x and the first derivative of x).

[Math. 6]

$$\ddot{\bar{x}}_i = K_p(\bar{x}_i - x_i) + K_v(\dot{\bar{x}}_i - \dot{x}_i) \tag{7}$$

Otherwise, by using the concept of a decomposed operation space, a target value related to an operation space expressed as a linear sum of other operation spaces (such as momentum, Cartesian relative coordinates, or linked joints) can also be set.

(2-1-1-2. Actual Force Computation Process)

In the second stage of the actual force computation process in generalized inverse dynamics, a process if conducted to replace the virtual force $f_v$ obtained by (2-1-1-1. Virtual force computation process) above with actual joint force and external force. A condition for realizing the generalized force $\tau_v = J_v^T f_v$ according to the virtual force with the generated torque $\tau_a$ generated in the joint sections and the external force $f_e$ is expressed by Formula (8) below.

[Math. 7]

$$\begin{bmatrix} J_{vu}^T \\ J_{va}^T \end{bmatrix} (f_v - \Delta f_v) = \begin{bmatrix} J_{eu}^T \\ J_{ea}^T \end{bmatrix} f_e + \begin{bmatrix} 0 \\ \tau_a \end{bmatrix} \tag{8}$$

Herein, the subscript a denotes the set of driven joint sections (driven joint set), while the subscript u denotes the set of non-driven joint sections (non-driven joint set). In other words, the upper part of Formula (8) above expresses the equilibrium of forces in the space according to the non-driven joint sections (non-driven joint space), while the lower part expresses the equilibrium of forces in the space according to the driven joint sections (driven joint space). $J_{vu}$ and $J_{va}$ are, respectively, the non-driven joint component and the driven joint component of the Jacobian related to the operation space in which the virtual force $f_v$ acts. $J_{eu}$ and $J_{ea}$ are, respectively, the non-driven joint component and the driven joint component of the Jacobian related to the operation space in which the external force $f_e$ acts. $\Delta f_v$ expresses the component of the virtual force $f_v$, which is not realizable by actual force.

The upper part of Formula (8) above is uncertain, and by solving a quadratic programming (QP) problem as indicated in Formula (9) below, for example, $f_e$ and $\Delta f_v$ can be obtained.

[Math. 8]

$$\min \frac{1}{2}\varepsilon^T Q_1 \varepsilon + \frac{1}{2}\xi^T Q_2 \xi \qquad (9)$$

$$\text{s.t.} \quad U\xi \geq v$$

Herein, ε is the difference between both sides of the upper part of Formula (8) above, and expresses the equality error of Formula (8). ξ is the concatenated vector of $f_e$ and $\Delta f_v$, and expresses a variable vector. $Q_1$ and $Q_2$ are positive definite symmetric matrices expressing weights for the case of minimization. Also, the inequality constraint in Formula (9) above is used to express a constraint condition related to the external force, corresponding to the set task, such as vertical reaction force, friction weighting, maximum value of the external force, and a support polygon.

For example, an equality constraint related to a rectangular support polygon is expressed in Formula (10) below.

[Math. 9]

$$|F_x| \leq \mu_t F_z,$$

$$|F_y| \leq \mu_t F_z,$$

$$F_z \geq 0,$$

$$|M_x| \leq d_y F_z,$$

$$|M_y| \leq d_x F_z,$$

$$|M_z| \leq \mu_r F_z \qquad (10)$$

Herein, z represents the normal direction of the contact plane, while x and y represent the two orthogonal tangent directions perpendicular to z. $(F_x, F_y, F_z)$ and $(M_x, M_y, M_z)$ are the external force and the external moment acting on the contact point. $\mu_t$ and $\mu_r$ are coefficients of friction related to translation and rotation, respectively. $(d_x, d_y)$ expresses the size of the support polygon.

For example, from Formulas (9) and (10) above, the minimum norm or the solution $f_e$, $\Delta f_v$ of the minimum error is computed. By substituting $f_e$ and $\Delta f_v$ obtained from Formula (9) above into Formula (8) above, the joint force $\tau_a$ required to realize the task, or in other words, the generated torque $\tau_a$ in each of the joint sections 511a to 511f can be obtained.

In actual practice, a constraint condition corresponding to the set task is set by appropriately formulation, like in Formula (10) above.

In the case of a system in which the bases are fixed, and there are no non-driven joints, all virtual forces are replaceable with joint forces only, and in Formula (8) above, $f_e=0$ and $\Delta f_v=0$ can be set. In this case, from the bottom part of Formula (8) above, the following Formula (11) can be obtained for the joint force $\tau_a$.

[Math. 10]

$$\tau_a = J_{va}^T f_v \qquad (11)$$

The above describes an example of whole body cooperative control using generalized inverse dynamics according to the present embodiment. As described above, by successively conducting a virtual force computation process and an actual force computation process, the joint force $\tau_a$ for achieving a desired task can be obtained. In other words, in the opposite sense, by treating a computed joint force $\tau_a$ as a control value for the driving control of the joint sections 511a to 511f, the joint sections 511a to 511f may be driven to achieve a desired task.

Note that regarding the whole body cooperative control using generalized inverse dynamics described so far, particularly details such as the process of deriving the virtual force $f_v$, the method of solving the above LCP to find the virtual force $f_v$, and the solution of the QP problem, literature such as JP 2009-95959A and JP 2010-188471A submitted previously by the applicant can be referenced, for example.

(2-1-2. Ideal Joint Control)

Next, ideal joint control according to the present embodiment will be described. The motion of the actuator 430 provided in each of the joint sections 511a to 511f of the support arm apparatus 500 is modeled by the equation of second-order lag motion expressed in Formula (12) below.

[Math. 11]

$$I_a \ddot{q}^{ref} = \tau_a + \tau_e - v_a \dot{q} \qquad (12)$$

Herein, q is the rotational angle of the actuator 430, $q^{ref}$ is a rotational angle target value of the actuator 430, $I_a$ is the inertial moment of the actuator 430, $\tau_a$ is the generated torque of the actuator 430, $\tau_e$ is the external torque acting on the actuator 430 from the outside, and $v_a$ is a viscous drag coefficient for the actuator 430. The above Formula (12) is a theoretical model expressing the motion of the actuator 430 in each of the joint sections 511a to 511f.

As described in (2-1-1. Generalized inverse dynamics) above, the torque $\tau_a$ that the actuator 430 in each of the joint sections 511a to 511f should generate (generated torque $\tau_a$) to realize a task can be computed with computation using generalized inverse dynamics. Consequently, ideally, by applying the generated torque $\tau_a$ computed for each actuator 430 to Formula (12) above, a response obeying the theoretical model expressed in Formula (12) above should be realized in each actuator 430, or in other words, the desired operation should be realized in the arm section 510.

However, in actuality, the influence of various disturbances causes error (modeling error) to occur between the actual motion in the actuator 430 and the theoretical model expressed in Formula (12) above in some cases. Modeling error may be divided roughly into error arising from mass properties, such as the mass, center of gravity, and inertia tensor of a multi-link structure (in other words, the arm section 510 to be controlled), and error arising from factors such as friction and inertia internal to the actuator 430. Of these, the former modeling error arising from mass properties may be reduced comparatively easily during construction of the theoretical model by increasing the precision of computer-aided design (CAD) data and applying identification techniques.

On the other hand, the latter modeling error arising from factors such as friction and inertia internal to the actuator 430 is caused by phenomena which are difficult to model, such as friction in the reduction gear 4264, for example. Consequently, when constructing a theoretical model illustrating the motion of the actuator 430, non-negligible modeling error may still remain. Additionally, there is also a possibility of error occurring between the values of the inertia $I_a$ and the viscous drag coefficient $v_a$ in Formula (12) above, and these values in the actual actuator 430. These difficult-to-model errors arising from factors such as friction and inertia internal to the actuator 430 may become disturbances in the driving control of the actuator 430. Thus, because of the influence of such disturbances, in actuality, cases occur in which the motion of the actuator does not respond exactly like the theoretical model expressed in Formula (12) above, or in other words, the desired operation is not realized.

Accordingly, in the present embodiment, an active control system is added to the actuator 430 to thereby correct the response of the actuator 430 to perform ideal response obeying the theoretical model expressed in Formula (12) above. Note that controlling the driving of the actuator 430 such that the actuators 430 of the support arm apparatus 500 (that is, the joint sections 511a to 511f) perform ideal response as expressed in Formula (12) above in this way is designated ideal joint control in the present embodiment.

Figure 3:
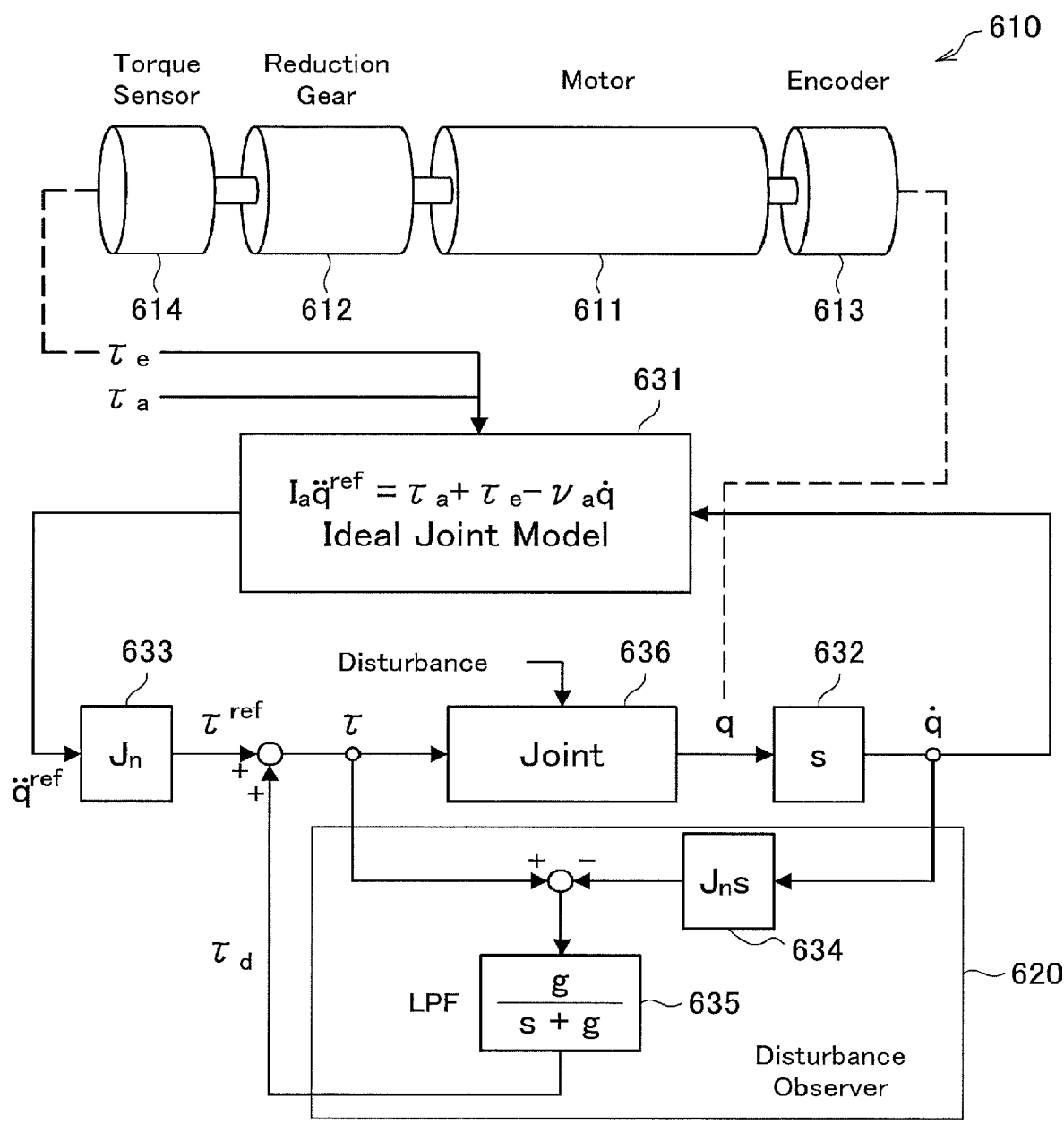
FIG. 3 is an explanatory diagram for explaining ideal joint control according to the present embodiment.

FIG. 3 will be referenced to describe ideal joint control according to the present embodiment in detail. FIG. 3 is an explanatory diagram for explaining ideal joint control according to the present embodiment. In FIG. 3, abstract computing elements that perform various mathematical operations related to ideal joint control are illustrated schematically as blocks. Note that the block diagram illustrated in FIG. 3 is an illustration of a series of processes for such ideal joint control with respect to the actuator 430 in one joint section among the joint sections 511a to 511f of the support arm apparatus 500.

Referring to FIG. 3, the actuator 610 illustrates a simulation of the functions of the actuator 430 illustrated in FIG. 2, for example. In FIG. 3, a motor 611, a reduction gear 612, an encoder 613, and a torque sensor 614 are illustrated as component members of the actuator 610. These respectively correspond to the motor 424, the reduction gear 426, the encoder 427, and the torque sensor 428 illustrated in FIG. 2.

The computing element 631 is a computing element that performs computations in accordance with the ideal joint model of the actuator 610 (that is, the joint sections 511a to 511f) expressed in Formula (12) above. The computing element 631 is able to take the generated torque $\tau_a$, the external torque $\tau_e$, and the rotational angular velocity (the first derivative of the rotational angle q) as input, and output the rotational angular acceleration target value (the second derivative of the rotational angle target value $q^{ref}$) expressed on the left side of Formula (12) above.

Herein, the actuator 610 performing response obeying the ideal model expressed in Formula (12) above means nothing other than that when the right side of Formula (12) above is given, the rotational angular acceleration on the left side is achieved. However, as above, ideal response obeying Formula (12) above actually is not produced sometimes, due to the influence of disturbances. Accordingly, in the present embodiment, a disturbance observer 620 is introduced. A process is conducted in which a disturbance estimate value $\tau_d$, which is an estimate value of the torque arising from a disturbance by the disturbance observer 620, is computed, and the disturbance estimate value $\tau_d$ is used to correct the calculation result by the computing element 631.

Hereinafter, specific processes will be described in order. First, the generated torque $\tau_a$ for realizing a desired task computed by the method described in (2-1-1. Generalized inverse dynamics) above, and the external torque $\tau_e$ detected by the torque sensor 614, are input into the computing element 631. Meanwhile, by inputting the rotational angle q of the actuator 610 detected by the encoder 613 into a computing element 632 that performs differential computations, the rotational angular velocity (the first derivative of the rotational angle q) of the actuator 610 is computed. By inputting the rotational angular velocity computed by the computing element 632, in addition to the generated torque $\tau_a$ and the external torque $\tau_e$ above, into the computing element 631, the rotational angular acceleration target value (the second derivative of $q^{ref}$) is computed by the computing element 631. The computed rotational angular acceleration target value is input into a computing element 633.

The computing element 633 is a computing element that computes the torque generated in the actuator 610, on the basis of the rotational angular acceleration of the actuator 610. In the present embodiment, specifically, the computing element 633 computes a torque target value $\tau^{ref}$ by multiplying the rotational angular acceleration target value computed by the computing element 631 by the nominal inertia $J_n$ of the actuator 610. In ideal response, the actuator 610 is driven to output the torque target value $\tau_{ref}$, and thus the desired operation should be realized, but as described earlier, the influence of disturbances and the like is produced in the actual response in some cases. Consequently, in the present embodiment, the torque target value $\tau^{ref}$ is corrected using the disturbance estimate value $\tau_d$ computed by the disturbance observer 620.

The configuration of the disturbance observer 620 will be described. The disturbance observer 620 computes the disturbance estimate value $\tau_d$, on the basis of the torque command value $\tau$ and the rotational angular velocity computed from the rotational angle q of the actuator 610 detected by the encoder 613. Herein, the torque command value $\tau$ is the command value ultimately given to the actuator 610 after the influence of disturbances is corrected. In other words, in the control system illustrated in FIG. 3, the actuator 610 is driven to output torque corresponding to the torque command value $\tau$. For example, in the case in which the disturbance estimate value $\tau_d$ is approximately zero, the torque command value $\tau$ becomes a value approximately equal to the torque target value $\tau^{ref}$.

Specifically, the disturbance observer 620 includes a computing element 634 and a computing element 635. The computing element 634 is a computing element that computes the torque generated in the actuator 610, on the basis of the rotational angular velocity of the actuator 610. Input into the computing element 634 is the rotational angular velocity computed by the computing element 632 on the basis of the rotational angle q detected by the encoder 613. The computing element 634 performs computations expressed by a transfer function $J_n s$ on the input rotational angular velocity, or in other words, finds the rotational angular acceleration by taking the derivative of the rotational angular velocity, and additionally multiplies the computed rotational angular acceleration by the nominal inertia $J_n$, and thereby computes an estimate value of the torque (torque estimate value) actually acting on the actuator 610.

Inside the disturbance observer 620, by taking the difference between the torque estimate value and the torque command value τ, the value of the torque due to a disturbance, that is, the disturbance estimate value $\tau_d$, is estimated. Specifically, the disturbance estimate value $\tau_d$ is the difference between the torque command value τ from the control in the previous step, and the torque estimate value from the control in the current step. Since the torque estimate value computed by the computing element 634 is based on an actual measured value, and the torque command value τ computed by the computing element 633 is based on an ideal theoretical model of the actuator 610 computed by the computing element 631, by taking the difference between the two, the influence of disturbances not taken into account by the theoretical model above can be estimated.

The computing element 635 is a computing element provided to prevent divergence of the system, and includes the function of a low-pass filter (LPF). The computing element 635 performs the computations expressed by the transfer function g/(s+g) to thereby output only the low-frequency component of an input value, and stabilize the system. The difference value between the torque estimate value and the torque target value $\tau^{ref}$ computed by the computing element 634 is input into the computing element 635, and the low-frequency component thereof is computed as the disturbance estimate value $\tau_d$.

After the disturbance estimate value $\tau_d$ is computed by the disturbance observer 620, the disturbance estimate value $\tau_d$ is added to the theoretical value, that is, the torque target value $\tau^{ref}$, to thereby compute the torque value to ultimately generate in the actuator 610, that is, the torque command value τ. The computed torque command value τ is input into a block 636 representing a joint section. The block 636 expresses a simulation of the joint sections 511a to 511f (in other words, the actuator 610). In the block 636, the actuator 610 is driven on the basis of the torque command value τ. Specifically, in the block 636, by converting the torque command value τ into a corresponding current value (current command value), and applying this current command value to the motor 611, the actuator 610 is driven to output torque corresponding to the torque command value τ.

By executing the process described above respectively for the actuator 430 in each of the joint sections 511a to 511f forming the arm section 510 of the support arm apparatus 500, each actuator 430 will exhibit the ideal response in accordance with the theoretical model, and the operation of the arm section 510 may be controlled highly precisely such that the arm section 510 achieves a desired task.

The above references FIG. 3 to describe ideal joint control according to the present embodiment. By adopting the configuration described above, in the driving control of the joint sections 511a to 511f according to the present embodiment, even in the case in which a disturbance component such as friction exists, it becomes possible to make the response of the actuator 610 track the target value.

Note that for details about the ideal joint control described above, literature such as JP 2009-269102 submitted previously by the applicant can be referenced, for example.

Herein, in the whole body cooperative control and the ideal joint control described above, the compensating torque by the gravity compensation mechanisms 540 and 550 are not taken into account. In other words, the whole body cooperative control and the ideal joint control described above express the control of the joint sections 511a to 511c and 511f not provided with the gravity compensation mechanisms 540 and 550. For the joint sections 511d and 511e provided with the gravity compensation mechanisms 540 and 550, in the whole body cooperative control described above, the compensating torque by the gravity compensation mechanisms 540 and 550 may be taken into account. (Note that in the ideal joint control, the compensating torque by the gravity compensation mechanisms 540 and 550 may also be taken into account. Details about such control will be described further in (5-1. Modification related to other control method) below.) Hereinafter, FIG. 4 will be referenced to describe such whole body cooperative control that accounts for the compensating torque by the gravity compensation mechanisms 540 and 550.

(2-2. Functional Configuration)

Figure 4:
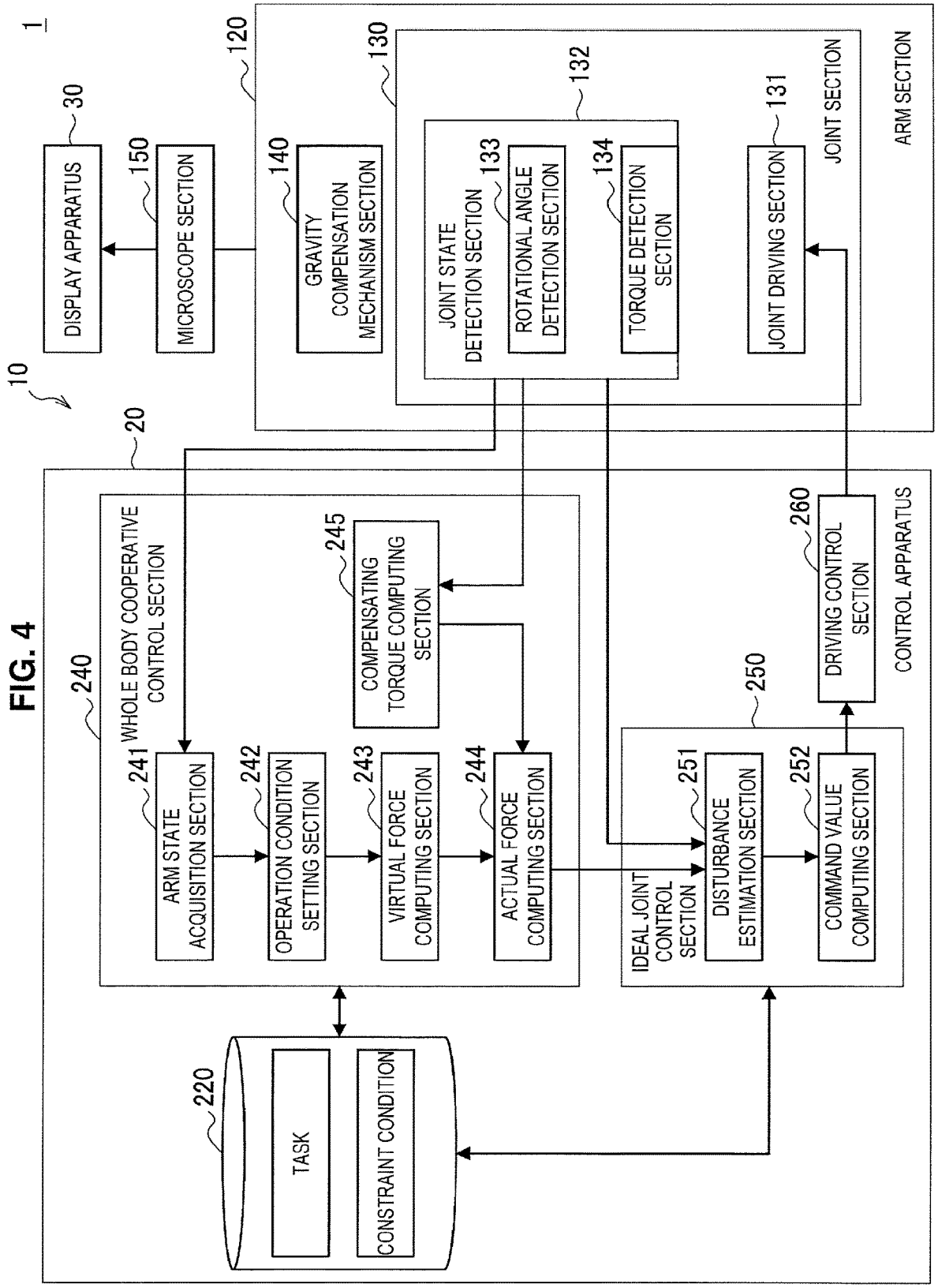
FIG. 4 is a block diagram illustrating an example of a functional configuration of a system and a support arm apparatus according to the present embodiment.

FIG. 4 will be referenced to describe a functional configuration of the system 1 and the support arm apparatus 500 according to the present embodiment illustrated in FIG. 1. FIG. 4 is a block diagram illustrating one example of a functional configuration of the system 1 and the support arm apparatus 500 according to the present embodiment. Note that in FIG. 4, for the sake of explanation, only functions that relate to the control of the operation of the arm section 510 are illustrated. Also, FIG. 4 illustrates a functional configuration for the case in which whole body cooperative control that accounts for the compensating torque by the gravity compensation mechanisms 540 and 550 is executed. In other words, the functional configuration illustrated in FIG. 4 is a functional configuration for controlling the driving of the joint sections 511d and 511e provided with the gravity compensation mechanisms 540 and 550. A functional configuration for controlling the driving of the other joint sections 511a to 511c and 511f corresponds to one in which the gravity compensation mechanism section 140 and the compensating torque computing section 245 described later are removed from the illustrated configuration.

Referring to FIG. 4, the system 1 according to the present embodiment includes a support arm apparatus 10 and a display apparatus 30. The support arm apparatus 10 and the display apparatus 30 correspond to the support arm apparatus 500 and the display apparatus 400 described with reference to FIG. 1, respectively. Since the functions of the display apparatus 30 have already been described with reference to FIG. 1, a description is omitted here.

(Support Arm Apparatus 10)

Referring to FIG. 4, the support arm apparatus 10 according to the present embodiment includes an arm section 120, a microscope section 150, and a control apparatus 20. The arm section 120, the microscope section 150, and the control apparatus 20 correspond to the arm section 510, the microscope section 520, and the control apparatus 530 of the support arm apparatus 500 described with respect to FIG. 1, respectively. Also, FIG. 4 illustrates a joint section 130 and a gravity compensation mechanism section 140 from among the configuration of the arm section 120 of the support arm apparatus 10. The joint section 130 and the gravity compensation mechanism section 140 correspond to the joint sections 511a to 511f and the gravity compensation mechanisms 540 and 550 of the arm section 510 described with respect to FIG. 1, respectively. Since the configurations and functions of the gravity compensation mechanism section 140 (that is, the gravity compensation mechanisms 540 and 550) and the microscope section 150 have already been described with reference to FIG. 1, a description is omitted here.

(Arm Section 120)

The joint section 130 of the arm section 120 includes a joint driving section 131 and a joint state detection section 132 as functions thereof.

The joint driving section 131 includes a driving mechanism for rotationally driving the joint section 130. The joint driving section 131 corresponds to the motor 424 and the motor driver 425 of the actuator 430 illustrated in FIG. 2. The driving of the joint driving section 131 is controlled by a driving control section 260 of the control apparatus 20 described later. Specifically, a value of torque (the torque command value $\tau$ illustrated in FIG. 3) that the joint section 130 needs to generate to achieve a desired task is computed by an ideal joint control section 250 of the control apparatus 20 described later. The driving control section 260 instructs the joint driving section 131 to drive the motor 424 in accordance with a current command value corresponding to the computed torque command value $\tau$. By driving the motor 424 included in the joint driving section 131 in accordance with the current command value, the joint section 130 is driven such that a torque corresponding to the torque command value $\tau$ is generated.

The joint state detection section 132 detects the state of the joint section 130. Herein, the state of the joint section 130 means the state of motion of the joint section 130. The state of the joint section 130 includes information such as the rotational angle, the rotational angular velocity, the rotational angular acceleration, and the torque of the joint section 130, for example.

The joint state detection section 132 includes a rotational angle detection section 133 that detects the rotational angle of the joint section 130 and a torque detection section 134 that detects the torque acting on the joint section 130. The rotational angle detection section 133 and the torque detection section 134 correspond to the encoder 427 and the torque sensor 428 of the actuator 430 illustrated in FIG. 2, respectively. For example, in the case in which the surgeon imparts an external force to the arm section 120 and/or the microscope section 150 to move the microscope section 150, the rotational angle, the rotational angular velocity, the rotational angular acceleration, the generated torque, and the like in the joint section 130 corresponding to the external force are detected by the joint state detection section 132.

The joint state detection section 132 provides information about the detected state of the joint section 130 to an arm state acquisition section 241, a compensating torque computing section 245, and a disturbance estimation section 251 of the control apparatus 20 described later.

(Control Apparatus)

The control apparatus 20 includes a whole body cooperative control section 240, an ideal joint control section 250, and a driving control section 260 as functions thereof. These functions are achieved by a processor included in the control apparatus 20 working in accordance with a predetermined program. Also, the control apparatus 20 is provided with a storage section 220 that stores various information processed by the control apparatus 20.

(Storage Section)

The storage section 220 stores various information processed by the control apparatus 20. In the present embodiment, the storage section 220 is able to store various parameters used in computations related to whole body cooperative control and ideal joint control performed by the whole body cooperative control section 240 and the ideal joint control section 250. For example, the storage section 220 stores tasks and constraint conditions used in computations related to whole body cooperative control by the whole body cooperative control section 240 described later. Also, the storage section 220 stores an internal model of the arm section 120 to use when the arm state acquisition section 241 acquires the arm state described later. Furthermore, the storage section 220 may also store computational results and numerical values or the like computed during the computational process as part of the computations related to the whole body cooperative control and ideal joint control. The whole body cooperative control section 240 and the ideal joint control section 250 are able to perform various processes while transmitting and receiving information to and from the storage section 220.

(Whole Body Cooperative Control)

The whole body cooperative control section 240 performs various mathematical operations related to whole body cooperative control using generalized inverse dynamics. The whole body cooperative control section 240 includes an arm state acquisition section 241, an operation condition setting section 242, a virtual force computing section 243, an actual force computing section 244, and a compensating torque computing section 245 as functions thereof.

The arm state acquisition section 241 acquires the state of the arm section 120 (arm state) on the basis of the state of the joint section 130 detected by the joint state detection section 132. Herein, the arm state means the state of motion of the arm section 120. For example, the arm state includes information about the position, velocity, acceleration, force, and the like of the arm section 120. By acquiring the arm state, the current position and attitude of the arm section 120 and the microscope section 150, as well as the current force acting on the arm section 120 and the microscope section 150, and the like may be grasped.

As described above, the joint state detection section 132 acquires information about the rotational angle, the rotational angular velocity, the rotational angular acceleration, the torque, and the like in each joint section 130 as the state of the joint section 130. In addition, an internal model of the arm section 120 is stored in the storage section 220 provided in the control apparatus 20. Herein, an internal model is a control model used for driving control of the support arm apparatus 10, and includes information (geometric information) expressing the position and the attitude of the arm section 120 to be controlled. The control apparatus 20 is able to acquire the current arm state on the basis of the state of the joint section 130 and the internal model.

The arm state acquisition section 241 provides information about the acquired arm state to the operation condition setting section 242.

The operation condition setting section 242 sets an operation condition for calculating the control torque (the generated torque $\tau_a$ described above) for driving control of the arm section 120 (that is, for driving control of the joint section 130). As the operation condition, a desired task to be executed by the arm section 120, a constraint condition corresponding to the task, and the like is set.

Specifically, combinations of various tasks settable for driving control of the arm section 120 and constraint conditions corresponding to each of these various tasks are stored in advance in the storage section 220 of the control apparatus 20. By accessing the storage section 220, the operation condition setting section 242 is able to set one these tasks and constraint conditions as an operation condition.

The tasks are various objectives related to the motion of the arm section 120. Specifically, tasks are preferably target values of the position and attitude (coordinates), velocity, acceleration, force, and the like of the arm section 120 (more specifically, the multiple joint sections 130 and the multiple links of the arm section 120) and the microscope section 150.

For example, the position and the attitude of the microscope section 150 when the surgeon has moved the position and the attitude of the microscope section 150 by a direct operation are set as a task (that is, a task is set causing the microscope section 150 to operate such that the microscope section 150 exists in the desired position and the attitude corresponding to the direction operation by the surgeon). Alternatively, a task causing the microscope section 150 to perform a pivot operation, a task causing the arm section 120 to perform a power assist operation, or the like may also be set.

Herein, a pivot operation is an operation in which, while the microscope section 150 is in a state of constantly facing a predetermined point in space (that is, in a state in which the optical axis of the microscope section 150 constantly passes through the predetermined point in space), the microscope section 150 moves over the surface of a cone whose apex is the predetermined point. In other words, with a pivot operation, the microscope section 150 performs a revolving operation that treats the axis of the cone whose apex is the predetermined point in space as the pivot. The predetermined point is also called the pivot point or the pivot center. In the exemplary configuration illustrated in FIG. 1, if the pivot center is set to the surgical site 341 of the patient 340, since the microscope section 150 will operate to revolve around the surgical site 341 while the microscope section 150 continues to capture the surgical site 341, it becomes possible to observe the surgical site 341 from a variety of directions.

Also, a power assist operation is an operation that controls the driving of the joint section 130 to support the movement of the arm section 120 and the microscope section 150 in the direction of a force imparted from the outside. Specifically, with a power assist operation, in the case in which an external torque is imparted to the arm section 120 and the microscope section 150 from the outside (for example, from the surgeon), the driving of each joint section 130 is controlled such that a generated torque in the same direction as the imparted external torque is generated in each joint section 130. By performing a power assist operation, in the case in which the surgeon causes the arm section 120 and the microscope section 150 to move by a direct operation, since the surgeon is able to cause the arm section 120 and the microscope section 150 to move with less force, operability for the surgeon may be improved.

Besides the above, any of various types of operations that may be set typically as tasks in a robot apparatus whose behavior is controlled by force control preferably are set as tasks.

The constraint conditions are various types of conditions that limit (constrain) the motion of the arm section 120. Specifically, the constraint conditions preferably are the coordinates of a region that each component member of the arm section 120 is prohibited from intruding into, a range of values (an upper limit value and/or a lower limit value) of the velocity and/or acceleration, a range of values (an upper limit value and/or a lower limit value) of the force that each component member produces, and the like when each component member moves.

For example, with respect to the above-described task of causing the microscope section 150 to operate such that the microscope section 150 exists in a desired position and attitude corresponding to a direct operation by the surgeon, an invasion prohibition region and an upper limit value on the movement speed of the arm section 120 and the microscope section 150 and the like preferably are set as a constraint condition. Alternatively, for example, with respect to the above-described task of causing the microscope section 150 to perform a pivot operation, a constraint condition is imposed on the position of the microscope section 150 such that the microscope section 150 is always positioned on the surface of the cone in the pivot operation.

Note that the range of limitation on various types of physical quantities in a constraint condition may be set as a range that may not be mechanically or controllably allowed on the basis of the structure of the arm section 120 and the like, or may be set appropriately by the surgeon from the perspective of safety and the like. For example, an attitude that is mechanistically impossible decided on the basis of the rotatable range and the like in each joint section 130 and an attitude at which control does not converge (what is called a singular configuration) decided according to the configuration of the arm section 120 preferably are set in the constraint conditions as prohibited attitudes for the arm section 120. With this arrangement, more stable control may be realized by the support arm apparatus 10. Also, for example, from the perspective of safety, an invasion prohibition region of the arm section 120 and the microscope section 150, an upper limit on the movement velocity, an upper limit on the generated torque in each joint section 130, and the like preferably are set as constraint conditions. With this arrangement, safer surgery may be realized.

Which task the arm section 120 is made to execute may be set appropriately by the surgeon via an input section (not illustrated) provided in the control apparatus 20, for example. The operation condition setting section 242, obeying an instruction input from the surgeon, is able to set a predetermined task and constraint condition as an operation condition.

The operation condition setting section 242 provides information about the arm state as well as information about the set task and constraint condition to the virtual force computing section 243.

The virtual force computing section 243 computes the virtual force that needs to act on each joint section 130 of the arm section 120 to execute the task set by the operation condition setting section 242. The virtual force computing section 243 computes the virtual force by executing the series of processes described in (2-1-1-1. Virtual force computation process) above. Since the content of this virtual force computation process has already been described, a detailed description is omitted.

The virtual force computing section 243 provides information about the computed virtual force to the actual force computing section 244.

The compensating torque computing section 245 computes the compensating torque by the gravity compensation mechanism section 140. As described with reference to FIG. 1, in the present embodiment, gravity compensation mechanism sections 140 (that is, the gravity compensation mechanisms 540 and 550) are provided in the joint section 511$d$ corresponding to the fourth axis $O_4$ and the joint section 511$e$ corresponding to the fifth axis $O_5$. These gravity compensation mechanism sections 140 includes the springs 542 and 552, and the restoring forces of the springs 542 and 552 produce a restoring torque corresponding to the rotational angle in the joint section 511$d$ and the joint section 511$e$. The compensating torque computing section 245 computes the value of the compensating torque produced by the gravity compensation mechanism section 140 in the current attitude of the arm section 120, on the basis of information about the rotational angle in the joint section 130 (the joint section 511d and the joint section 511e) transmitted from the joint state detection section 132.

Specifically, when described by taking the gravity compensation mechanism 540 as an example, the restoring force $F_s$ by the spring 542 included in the gravity compensation mechanism 540 can be expressed as a function of the rotational angle q in the joint section 511d as in Formula (13) below.

[Math. 12]

$$F_s(q) = f_0 + k(l(q) - l_0) \qquad (13)$$

Herein, $f_0$ is the initial tension force of the spring 542 (that is, the restoring force that the spring 542 is generating when q=0), k is the spring constant of the spring 542, l(q) is the length of the spring 542 expressed as a function of the rotational angle q, and $l_0$ is the initial length of the spring 542 (that is, the length of the spring 542 when q=0). l(q) and $l_0$ may be computed by geometric examination according to the structure of the arm section 120 (more specifically, the structure of the gravity compensation mechanism 540 and the positional relationship between the joint section 511d and the gravity compensation mechanism 540). Also, k is a known constant dependent on the properties of the spring 542, and $f_0$ may be computed from the spring constant k and the initial length $l_0$.

Also, if D is taken to be the moment arm for the restoring torque, then D can be expressed as a function D(q) of the rotational angle in the joint section 511d. D(q) likewise may be computed by geometric examination according to the structure of the arm section 120 (more specifically, the structure of the gravity compensation mechanism 540 and the positional relationship between the joint section 511d and the gravity compensation mechanism 540).

Consequently, the compensating torque $G_m(q)$ by the gravity compensation mechanism 540 can be expressed using Formula (13) above and the moment arm D(q), as in Formula (14) below.

[Math. 13]

$$G_m(q) = F_s(q) \times D(q) \qquad (14)$$

The compensating torque computing section 245 is able to use Formula (14) above to compute the value of the compensating torque produced by the gravity compensation mechanism 540 in the current attitude of the arm section 120. Similarly, since the compensating torque produced by the gravity compensation mechanism 550 can also be expressed as a function of the rotational angle in the joint section 511e, the compensating torque computing section 245 is able to use the function to compute the value of the compensating torque produced by the gravity compensation mechanism 550 in the current attitude of the arm section 120.

The compensating torque computing section 245 provides the computed value of the compensating torque produced by the gravity compensation mechanism section 140 (gravity compensation mechanisms 540 and 550) in the current attitude of the arm section 120 to the actual force computing section 244.

The actual force computing section 244 computes the actual force that actually needs to act on each joint section 130 of the arm section 120 to execute the task set by the operation condition setting section 242, on the basis of the virtual force computed by the virtual force computing section 243. The actual force computing section 244 computes the actual force by executing the series of processes described in (2-1-1-2. Actual force computation process) above. At this time, in this process, the actual force computing section 244 computes the actual force while accounting for the compensating torque by the gravity compensation mechanism section 140.

Specifically, since the arm section 120 is a system in which the bases are fixed and there are no non-driven systems, in the process of computing the actual force for the arm section 120, Formula (8) above is expressed as in Formula (11) above. Consequently, the actual force computing section 244 uses the virtual force $f_v$ computed by the virtual force computing section 243 to compute the actual force, or in other words the generated torque $\tau_a$, for each joint section 130 in accordance with Formula (11) above. The generated torque $\tau_a$ calculated at this point includes the torque for gravity compensation needed in the case in which the gravity compensation mechanism section 140 is not provided (that is, the torque for canceling out the load torque G due to the self-weight of the arm section 120). Note that since the load torque G due to the self-weight of the arm section 120 acting on each joint section 130 is different depending on the attitude of the arm section 120, the value of the torque for gravity compensation included in the generated torque $\tau_a$ may be computed as a different value every control cycle of the whole body cooperative control section 240 (that is, the cycle of computing the generated torque $\tau_a$).

For the joint sections 130 not provided with the gravity compensation mechanism section 140 (given the exemplary configuration illustrated in FIG. 1, the joint sections 511a, 511b, 511c, and 511f), the actual force computing section 244 treats the generated torque $\tau_a$ computed according to Formula (11) above directly as the actual force (generated torque) in these joint sections 130. On the other hand, for the joint sections 130 provided with the gravity compensation mechanism section 140 (given the exemplary configuration illustrated in FIG. 1, the joint sections 511d and 511e), the actual force computing section 244 subtracts the compensating torque computed by the compensating torque computing section 245 from the generated torque $\tau_a$ computed according to Formula (11) above, and treats this value as the actual force (generated torque) in these joint sections 130. According to such a process, the generated torque ultimately computed for these joint sections 130 includes, as the gravity compensation component, only the part that cannot be fully covered by the compensating torque from the gravity compensation mechanism section 140 out of the torque for canceling out the load torque G due to the self-weight of the arm section 120.

The actual force computing section 244 provides information about the computed actual force, or in other words the generated torque $\tau_a$ that should be generated in each joint section 130, to the ideal joint control section 250.

(Ideal Joint Control Section)

The ideal joint control section 250 performs various mathematical operations related to ideal joint control. The ideal joint control section 250 includes a disturbance estimation section 251 and a command value computing section 252 as functions thereof. Note that the processes performed by the ideal joint control section 250 correspond to the series of processes described in (2-1-2. Ideal joint control) above.

The disturbance estimation section 251 includes functions corresponding to the disturbance observer 620 illustrated in FIG. 3. The disturbance estimation section 251 computes the value of the torque due to the disturbance, namely a disturbance estimation value $\tau_d$, by taking the difference between the torque command value τ (the torque value acting on the joint section 130, which is computed in accordance with the theoretical model of the joint section 130 illustrated in Formula (12) above on the basis of the generated torque $\tau_a$ computed by the actual force computing section 244 and the external torque value acting on the joint section 130 detected by the rotational angle detection section 133), and the torque value acting on the joint section 130 computed on the basis of the rotational angle of the joint section 130 detected by the rotational angle detection section 133. Note that the torque command value τ referred to here is a command value expressing the torque to be generated ultimately by the joint section 130 of the arm section 120. The torque command value τ used by the disturbance estimation section 251 to compute the disturbance estimation value $\tau_d$ may be the torque command value τ in the control of the previous step.

The command value computing section 252 uses the disturbance estimation value $\tau_d$ computed by the disturbance estimation section 251 to compute the torque command value τ, which is a command value expressing the torque to be generated ultimately by the joint section 130 of the arm section 120. Specifically, the command value computing section 252 computes the torque command value τ by adding the disturbance estimation value $\tau_d$ computed by the disturbance estimation section 251 to the torque target value $\tau^{ref}$ computed from the theoretical model of the joint section 130 illustrated in Formula (12) above.

The command value computing section 252 provides information about the computed torque command value τ to the driving control section 260.

(Driving Control Section)

On the basis of the torque command value τ computed by the command value computing section 252, the driving control section 260 controls the driving of the joint driving section 131 of the joint section 130 such that a torque corresponding to the torque command value τ is generated in the joint section 130. Specifically, the driving control section 260 converts the torque command value τ into a corresponding current command value, and instructs the motor driver 425 included in the joint driving section 131 to drive the motor 424 included in the joint driving section 131 by the current corresponding to the current command value. By the control from the driving control section 260, each joint section 130 included in the arm section 120 is driven such that a torque corresponding to the torque command value τ computed by the ideal joint control section 250 is generated, and therefore the arm section 120 is driven such that a desired task is achieved while also performing gravity compensation for the component not fully compensated by the gravity compensation mechanism section 140.

The above references FIG. 4 to describe a functional configuration of the system 1 and the support arm apparatus 10 according to the present embodiment.

Herein, the control cycle of the whole body cooperative control section 240 (that is, the cycle of computing the generated torque $\tau_a$) and the control cycle of the ideal joint control section 250 (that is, the cycle of computing the torque command value τ) do not necessarily have to be the same. For example, as described above, the whole body cooperative control section 240 computes the generated torque $\tau_a$ in each joint section 130 to achieve a desired task, but in the case in which additional external force is not imparted to the arm section 120 and the microscope section 150, and the position and attitude do not change, the generated torque $\tau_a$ in each joint section 130 is thought to stay approximately constant. Consequently, although dependent on the content of the task and the use of the support arm apparatus 10, it is not strictly necessary to recalculate the generated torque $\tau_a$ frequently. Therefore, it is conceivable that the control cycle of the whole body cooperative control section 240 may also be relatively long.

On the other hand, as described above, the ideal joint control section 250 accounts for the influence of a disturbance to compute the torque command value τ such that the joint section 130 will exhibit ideal response. Consequently, if one is attempting to compute the torque command value τ precisely in correspondence with a disturbance that changes from moment to moment, it is preferable to execute the computation of the torque command value on a relatively short cycle. In other words, a relatively short control cycle of the ideal joint control section 250 is thought to be preferable.

In this way, the control cycle demanded of the whole body cooperative control section 240 and the control cycle demanded of the ideal joint control section 250 may be different in some cases. Consequently, the control apparatus 20 may be configured such that the control cycles of the whole body cooperative control section 240 and the ideal joint control section 250 are different from each other, specifically such that the control cycle of the ideal joint control section 250 is shorter than the control cycle of the whole body cooperative control section 240.

Figure 6:
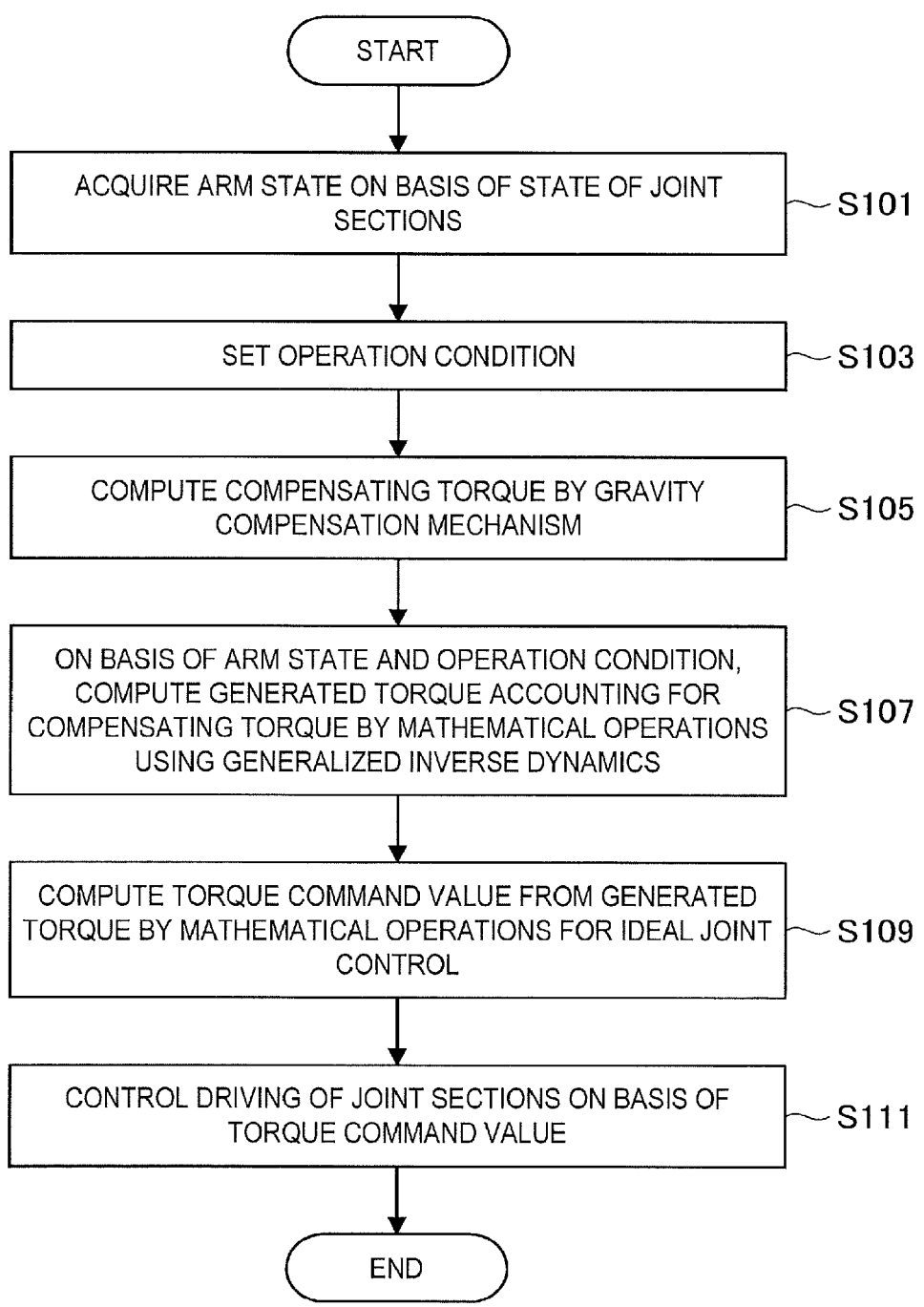
FIG. 6 is a flowchart illustrating an example of a processing procedure of a method of controlling an arm section of a support arm apparatus according to the present embodiment.

Note that the functional configuration illustrated in FIG. 6 is merely one example of a functional configuration of the system 1 and the support arm apparatus 10 according to the present embodiment, and the functional configuration of the system 1 and the support arm apparatus 10 is not limited to such an example. It is sufficient for the system 1 and the support arm apparatus 10 to be capable of realizing the functions described above, and any typically conceivable configuration may be taken.

For example, besides the functions illustrated, the support arm apparatus 10 preferably includes various functions included in a typical support arm apparatus (observation apparatus). For example, as described above, the support arm apparatus 10 may include functions such as an input section by which the surgeon inputs various information into the support arm apparatus 10. The input section may include various input devices such as a mouse, a touch panel, a button, a switch, a lever, and the like, for example. Since functions omitted from illustration preferably are similar to functions provided in a typical support arm apparatus (observation apparatus), a detailed description is omitted.

Also, for example, the functions provided in the control apparatus 20 of the support arm apparatus 10 do not all have to be executed in a single apparatus, and may also be executed by the cooperation of multiple apparatus. For example, by communicably connecting a single apparatus including only any one or multiple functions from among the functions included in the whole body cooperative control section 240, the ideal joint control section 250, and the driving control section 260 to another apparatus including the other functions, the same functions as the illustrated control apparatus 20 may be realized.

Additionally, it is possible to develop a computer program for realizing each function of the system 1, particularly the control apparatus 20 of the support arm apparatus 10, according to the present embodiment illustrated in FIG. 4, and implement the computer program in a processing apparatus such as a PC. In addition, a computer-readable recording medium storing such a computer program may also be provided. The recording medium may be a magnetic disk, an optical disc, a magneto-optical disc, flash memory, or the like, for example. Furthermore, the above computer program may also be delivered via a network, for example, without using a recording medium.

3. EXAMPLE DESIGN OF SPRING IN GRAVITY COMPENSATION MECHANISM

A specific example design of the springs 542 and 552 of the gravity compensation mechanisms 540 and 550 according to the present embodiment illustrated in FIG. 1 will be described. Herein, as one example, a specific example design of the gravity compensation mechanism 540 provided in the joint section 511d will be described.

As described with reference to Formula (14) above, the length l(q) of the spring 542 of the gravity compensation mechanism 540 can be expressed as a function of the rotational angle q in the joint section 511d. On the other hand, as described above in the description of the functions of the actual force computing section 244 illustrated in FIG. 4, the load torque G(q) due to the self-weight of the arm section 510 acting on the joint section 511d and the compensating torque $G_m(q)$ by the gravity compensation mechanism 540 may also be expressed as functions of the rotational angle q in the joint section 511d. Consequently, from l(q), G(q), and $G_m(q)$, it is possible to compute the properties (the relationship between length (the amount of extension or contraction) and restoring force) of an ideal spring 542 such that the load torque G(q) may be canceled out completely by the compensating torque $G_m(q)$ arising from the restoring force of the spring 542.

Figure 5:
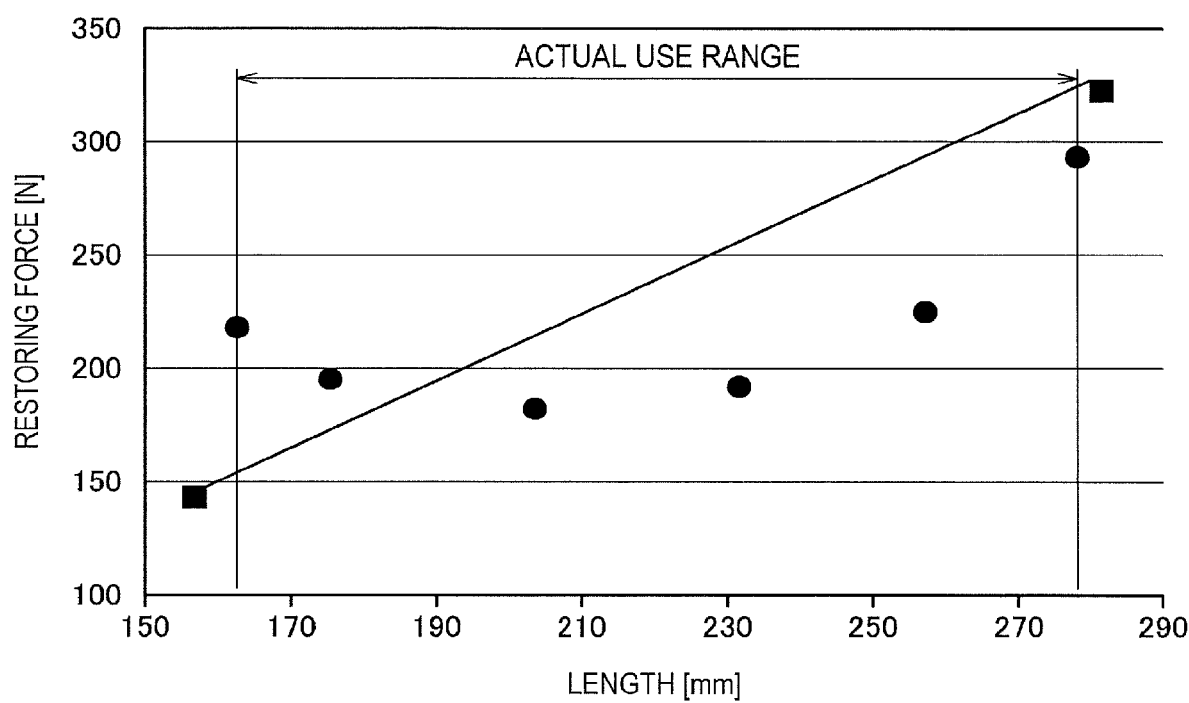
FIG. 5 is a diagram illustrating an example of ideal properties of a spring of a gravity compensation mechanism.

FIG. 5 is a diagram illustrating an example of the ideal properties of the spring 542 of the gravity compensation mechanism 540. In FIG. 5, the length l(q) of the spring 542 takes the horizontal axis, the restoring force that the spring 542 needs to generate to completely cancel out the load torque G(q) for a given length l(q) takes the vertical axis, and the relationship between the two is plotted with circular markers.

As illustrated in FIG. 5, the properties of the ideal spring 542 do not necessarily become linear, and it is impossible to fabricate a spring 542 having such properties in reality. Consequently, in the present embodiment, an actual use range of the rotational angle q of the joint section 511d is set as a range of angles with high use frequency, the properties of the ideal spring 542 is approximated linearly in an actual use range of the length l(q) of the spring 542 corresponding to the actual use range of the rotational angle q, and a spring having the properties indicated by such an approximation line is used as the spring 542 of the gravity compensation mechanism 540. In this case, it is preferable to account for margins, and perform the linear approximation over a wider range than the actual use range. In FIG. 5, the approximation line for such a linear approximation is illustrated as well (with mock square markers attached at both ends of the approximation line).

In the case of configuring the gravity compensation mechanism 540 using a spring 542 having such properties, the difference between the circular markers indicating the ideal restoring force and the approximation line illustrated in FIG. 5 corresponds to the force not fully covered by the gravity compensation mechanism 540 out of the load torque G(q). In the present embodiment, gravity compensation is performed by covering for this insufficiency with the generated torque of the actuator 430 provided in the joint section 511d.

Herein, an example design of the gravity compensation mechanism 540 is described as one example, but it is sufficient to design the spring 552 similarly for the gravity compensation mechanism 550. Note that in actuality, l(q) and $G_m(q)$ described above are expected to be different for each support arm apparatus 500 due to assembly error and the like of the gravity compensation mechanism 540. Consequently, by performing a process of computing l(q) and $G_m(q)$ for each support arm apparatus 500 and designing the springs 542 and 552 on the basis of the result, it becomes possible to design the springs 542 and 552 more precisely. However, this case requires fabricating different springs 542 and 552 for each support arm apparatus 500, and therefore is not preferable from a mass productivity standpoint. Consequently, to avoid such a situation, the gravity compensation mechanisms 540 and 550 may be provided with a mechanism that adjusts the tension positions of the springs 542 and 552. By using such a mechanism to appropriately adjust the tension positions of the springs 542 and 552 such that predetermined l(q) and $G_m(q)$ are realized, it becomes possible to use springs 542 and 552 having the same properties to achieve the desired properties like the approximation line illustrated in FIG. 5, by which manufacturing costs can be decreased further, and which is also favorable from a mass productivity standpoint.

4. CONTROL METHOD OF SUPPORT ARM APPARATUS

Referring to FIG. 6, a processing sequence of a control method of the arm section 120 of the support arm apparatus 10 according to the present embodiment will be described. FIG. 6 is a flowchart illustrating an example of a processing sequence of a control method of the arm section 120 of the support arm apparatus 10 according to the present embodiment.

Note that each process illustrated in FIG. 6 corresponds to each process executed by the control apparatus 20 of the support arm apparatus 10 illustrated in FIG. 5. In other words, by having a processor included in the control apparatus 20 operate in accordance with a predetermined program, each process illustrated in FIG. 6 is executed. Since the details of each process illustrated in FIG. 6 already have been described in (2-2. Functional configuration) above, in the following description of the processing sequence of the control method, an overview of each process will be described briefly, but a detailed description will be omitted.

Referring to FIG. 6, in the control method of the arm section 120 of the support arm apparatus 10 according to the present embodiment, first, the arm state is acquired on the basis of the state of the joint section 130 (step S101). At this point, the state of the joint section 130 is the rotational angle, generated torque, and the like of the joint section 130 detected by the joint state detection section 132 illustrated in FIG. 5, for example. In addition, the arm state is the state of motion of the arm section 120, and is the position, velocity, acceleration, force, and the like of the arm section 120, for example. The process illustrated in step S101 corresponds to the process executed by the arm state acquisition section 241 illustrated in FIG. 5.

Next, an operation condition is set (step S103). In step S103, for example, a task specified by the user and a constraint condition corresponding to the task are set as an operation condition for calculating a control value (the generated torque $\tau_a$ described above) for driving the arm section 120 to execute the task. The process illustrated in step S103 corresponds to the process executed by the operation condition setting section 242 illustrated in FIG. 5.

Next, the compensating torque by the gravity compensation mechanism section 140 is computed (step S105). In step S105, for example, the compensating torque $G_m(q)$ by the gravity compensation mechanism section 140 illustrated in Formula (14) above is computed on the basis of the rotational angle of the joint section 130 detected by the joint state detection section 132 illustrated in FIG. 5. The process illustrated in step S105 corresponds to the process executed by the compensating torque computing section 245 illustrated in FIG. 5.

Next, on the basis of the arm state and the operation condition, mathematical operations for whole body cooperative control using generalized inverse dynamics are performed, and the generated torque $\tau_a$ in the joint sections 130 is computed (step S107). In step S107, first, the virtual force that needs to act on each joint section 130 of the arm section 120 to execute the task set in step S103 is computed. Next, on the basis of the computed virtual force, the actual force that actually needs to act on each joint section 130 of the arm section 120 to execute the task set in step S103 is computed, and the generated torque $\tau_a$ in each joint section 130 is computed. At this time, the generated torque $\tau_a$ is computed while also taking into account the compensating torque computed in step S105 (that is, by subtracting the compensating torque computed in step S105 from the load torque due to the self-weight of the arm section 120, and treating the result as the gravitational component due to the self-weight of the arm section 120). With this arrangement, there is computed a generated torque $\tau_a$ that should be generated in the joint sections 130 so that the task set in step S103 may be executed, while also compensating for the gravitational component that is not fully compensated by the gravity compensation mechanism section 140. The process illustrated in step S107 corresponds to the processes executed by the virtual force computing section 243 and the actual force computing section 244 illustrated in FIG. 5.

Next, mathematical operations for ideal joint control are performed, and the torque command value $\tau$ is computed from the generated torque $\tau_a$ (step S109). In step S109, specifically, a torque value due to a disturbance, namely the disturbance estimate value $\tau_d$ is computed, and the disturbance estimate value $\tau_d$ is used to compute the torque command value $\tau$, which is a command value expressing the torque to be generated ultimately in the joint sections 130 of the arm section 120. The process illustrated in step S109 corresponds to the process executed by the ideal joint control section 250 illustrated in FIG. 5.

Next, on the basis of the computed torque command value $\tau$, the driving of the joint sections 130 of the arm section 120 is controlled (step S111). With this arrangement, the arm section 120 is driven such that the task set in step S103 may be executed, while also compensating for the gravitational component that is not fully compensated by the gravity compensation mechanism section 140. The process illustrated in step S111 corresponds to the process executed by the driving control section 260 illustrated in FIG. 5.

The above references FIG. 6 to describe a processing sequence of a control method of the support arm apparatus 10 according to the present embodiment.

5. MODIFICATIONS

Several modifications of the embodiment described above will be described.
(5-1. Modification Related to Other Control Method)
In the embodiment described above, as described with reference to FIG. 5, the compensating torque is taken into account when computing the actual force (that is, the generated torque $\tau_a$). However, the present embodiment is not limited to such an example. For example, the process of taking the compensating torque into account may also be performed when computing the torque command value $\tau$ in the ideal joint control section 250.

Figure 7:
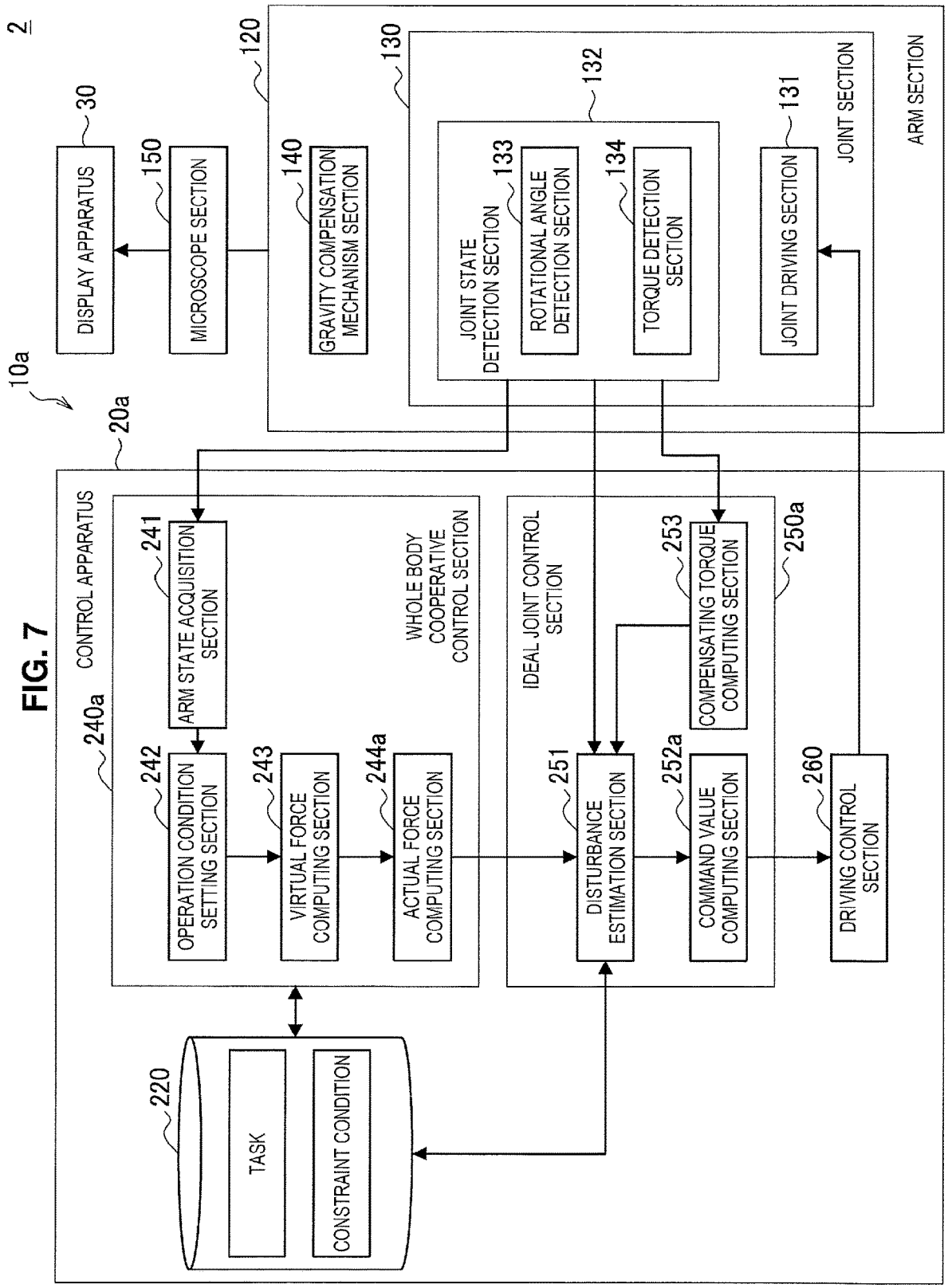
FIG. 7 is a block diagram illustrating an example of a functional configuration of a system and a support arm apparatus according to a modification with a different control method.

FIG. 7 will be referenced to describe a functional configuration of a system and the support arm apparatus according to a modification with such a different control method. FIG. 7 is a block diagram illustrating an example of a functional configuration of a system and a support arm apparatus according to a modification with a different control method. In FIG. 7, similarly to FIG. 4, only functions that relate to the control of the operation of the arm section of the support arm apparatus are illustrated. Also, in FIG. 7, similarly to FIG. 4, a functional configuration for controlling the driving of the joint sections 511d and 511e provided with the gravity compensation mechanisms 540 and 550 is illustrated.

Referring to FIG. 7, the system 2 according to the present modification includes a support arm apparatus 10a and the display apparatus 30. Additionally, the support arm apparatus 10a includes the arm section 120, the microscope section 150, and a control apparatus 20a. Herein, the system 2 corresponds to a modification of the functional configuration of the control apparatus 20 of the support arm apparatus 10 in the system 1 described with reference to FIG. 5. Since other functions in the system 2 are similar to system 1, a description is omitted here.

Referring to FIG. 7, the control apparatus 20a according to the present modification includes a whole body cooperative control section 240a, an ideal joint control section 250a, and the driving control section 260 as functions thereof. These functions are achieved by a processor included in the control apparatus 20a working in accordance with a predetermined program. Also, the control apparatus 20a is provided with a storage section 220 that stores various information processed by the control apparatus 20a. Since the functions of the driving control section 260 and the storage section 220 are similar to these functions in the control apparatus 20 illustrated in FIG. 5, a description is omitted here.

The whole body cooperative control section 240a performs various mathematical operations related to whole body cooperative control using generalized inverse dynamics. The whole body cooperative control section 240a includes the arm state acquisition section 241, the operation condition setting section 242, the virtual force computing section 243, and an actual force computing section 244a as functions thereof. In this way, the whole body cooperative control section 240a corresponds to a modification of the whole body cooperative control section 240 illustrated in FIG. 5, in which the functions of the compensating torque computing section 245 are removed, and the functions of the actual force computing section 244 are modified accordingly.

In the whole body cooperative control section 240a, the functions of the arm state acquisition section 241, the operation condition setting section 242, and the virtual force computing section 243 are similar to these functions in the control apparatus 20 illustrated in FIG. 5. In the present modification, in the whole body cooperative control section 240a, the process of computing the compensating torque is not performed, and the actual force computing section 244a executes the series of processes described in in (2-1-1-2. Actual force computation process) above without taking the compensating torque into account to thereby compute the generated torque $\tau_a$. In other words, the generated torque $\tau_a$ computed at this point includes the torque for gravity compensation needed in the case in which the gravity compensation mechanism section 140 is not provided (that is, the torque for canceling out the load torque G due to the self-weight of the arm section 120). The actual force computing section 244*a* provides information about the computed generated torque $\tau_a$ to the ideal joint control section 250*a*.

The ideal joint control section 250*a* performs various mathematical operations related to ideal joint control. The ideal joint control section 250*a* includes the disturbance estimation section 251, the command value computing section 252, and a compensating torque computing section 253 as functions thereof. In this way, the ideal joint control section 250*a* corresponds to adding the function of the compensating torque computing section 253 to the ideal joint control section 250 illustrated in FIG. 5. The ideal joint control section 250*a* computes the torque command value $\tau$ by executing the series of processes described in (2-1-2. Ideal joint control) above, but in the present modification, at this point, the ideal joint control section 250*a* computes the torque command value $\tau$ by taking the compensating torque by the gravity compensation mechanism section 140 into account.

Specifically, in the ideal joint control section 250*a*, the function of the compensating torque computing section 253 is similar to the function of the compensating torque computing section 245 illustrated in FIG. 4. The compensating torque computing section 253 uses Formula (14) above to compute the value of the compensating torque produced by the gravity compensation mechanism section 140 in the current attitude of the arm section 120. The compensating torque computing section 253 provides the computed value of the compensating torque produced by the gravity compensation mechanism section 140 (gravity compensation mechanisms 540 and 550) in the current attitude of the arm section 120 to the disturbance estimation section 251.

The functions of the disturbance estimation section 251 and the command value computing section 252 are similar to these functions illustrated in FIG. 4. In other words, the disturbance estimation section 251 computes the value of the torque due to a disturbance, that is, the disturbance estimation value $\tau_d$. Also, the command value computing section 252 uses the disturbance estimation value $\tau_d$ computed by the disturbance estimation section 251 to compute the torque command value $\tau$, that is, the command value expressing the torque to be generated ultimately by the joint section 130 of the arm section 120. However, in the present modification, at this point, instead of using the generated torque $\tau_a$ computed by the actual force computing section 244*a*, the disturbance estimation section 251 uses the value obtained by subtracting the compensating torque computed by the compensating torque computing section 253 from the generated torque $\tau_a$ as the input value. In other words, in the present modification, the disturbance estimation section 251 and the command value computing section 252 perform processes similar to the embodiment described above, except for using the value obtained by subtracting the compensating torque computed by the compensating torque computing section 253 from the generated torque $\tau_a$ instead of the generated torque $\tau_a$ computed by the actual force computing section 244*a* as the input value. With this arrangement, a torque command value $\tau$ taking the compensating torque by the gravity compensation mechanism section 140 into account may be computed.

The command value computing section 252 provides information about the computed torque command value $\tau$ to the driving control section 260. On the basis of the torque command value $\tau$ computed by the command value computing section 252, the driving control section 260 controls the driving of the joint driving section 131 of the joint section 130 such that a torque corresponding to the torque command value $\tau$ is generated. With this arrangement, the arm section 120 is driven such that a desired task is achieved while also performing gravity compensation for the component not fully compensated by the gravity compensation mechanism section 140.

The above describes a functional configuration of the system 2 and the support arm apparatus 10*a* according to a modification with a different control method. As in the present modification, even if the compensating torque is taken into account in the mathematical operations related to ideal joint control rather than the mathematical operations related to whole body cooperative control, a torque command value $\tau$ accounting for the compensating torque can be computed as the ultimate torque command value $\tau$ for the actuators 430, making it possible to control the operation of the arm section 120 in a similar manner.

Herein, as described in (2-2. Functional configuration) above, in the control apparatus 20 and 20*a*, the control cycle of mathematical operations related to ideal joint control (that is, the cycle of computing the torque command value $\tau$) may be set shorter than the control cycle of mathematical operations related to whole body cooperative control (that is, the cycle of computing the generated torque $\tau_a$). In other words, the ideal joint control sections 250 and 25*a* may feature a relatively short control cycle.

On the other hand, the mathematical operations related to whole body cooperative control tend to be more compute-intensive compared to the mathematical operations related to ideal joint control. Consequently, in the present embodiment, to make intensive computations processable, more memory may be allocated to the hardware included in the whole body cooperative control sections 240 and 240*a*. In this way, in brief, the whole body cooperative control sections 240 and 240*a* may feature the ability to process intensive computations favorably.

In this way, the whole body cooperative control sections 240 and 240*a* may feature different computational processing capabilities from the ideal joint control sections 250 and 250*a*. Consequently, whether to include the functions of the compensating torque computing sections 245 and 253 in the whole body cooperative control sections 240 and 240*a* or in the ideal joint control sections 250 and 250*a* (that is, whether to make the functional configuration of the control apparatus 20 and 20*a* configured like the embodiment illustrated in FIG. 4 or configured like the modification illustrated in FIG. 7) preferably is decided appropriately in consideration of the computational processing features of such whole body cooperative control sections 240 and 240*a* and also such ideal joint control sections 250 and 250*a*. For example, to raise the accuracy of the gravity compensation further, in the case of attaching importance to executing the mathematical operations related to gravity compensation on a shorter cycle, like the functional configuration illustrated in FIG. 7, it is preferable to include the functions of the compensating torque computing section 253 in the ideal joint control section 250*a*, and have the ideal joint control section 250*a* execute the process of computing the torque command value $\tau$ that accounts for the compensating torque computed by the compensating torque computing section 253 on a short cycle. On the other hand, for example, in the case in which the accuracy of the gravity compensation is not demanded as much, like the functional configuration illustrated in FIG. 4, it is preferable to include the functions of the compensating torque computing section 253 in the whole body cooperative control section 240 capable of processing more intensive computations, and have the whole body cooperative control section 240 execute the process of computing the generated torque $\tau_a$ that accounts for the compensating torque computed by the compensating torque computing section 253.

(5-2. Modification Related to Hanging Support Arm Apparatus)

In the embodiment described above, as described with reference to FIG. 1, the support arm apparatus 500 is configured such that the base end of the arm section 510 is connected to a base section (not illustrated in FIG. 1) installed on the floor, and the arm section 510 extends from the base section. However, the present embodiment is not limited to such an example. It is sufficient to configure the support arm apparatus 500 such that the medical tool attached to the front end of the arm section 510 is controllable to be at a desired position and attitude corresponding to the use of the medical tool, and the configuration of the support arm apparatus 500 may be any configuration. For example, the support arm apparatus 500 may also be what is called a hanging support arm apparatus in which the arm section 510 hangs down from the ceiling.

Figure 8:
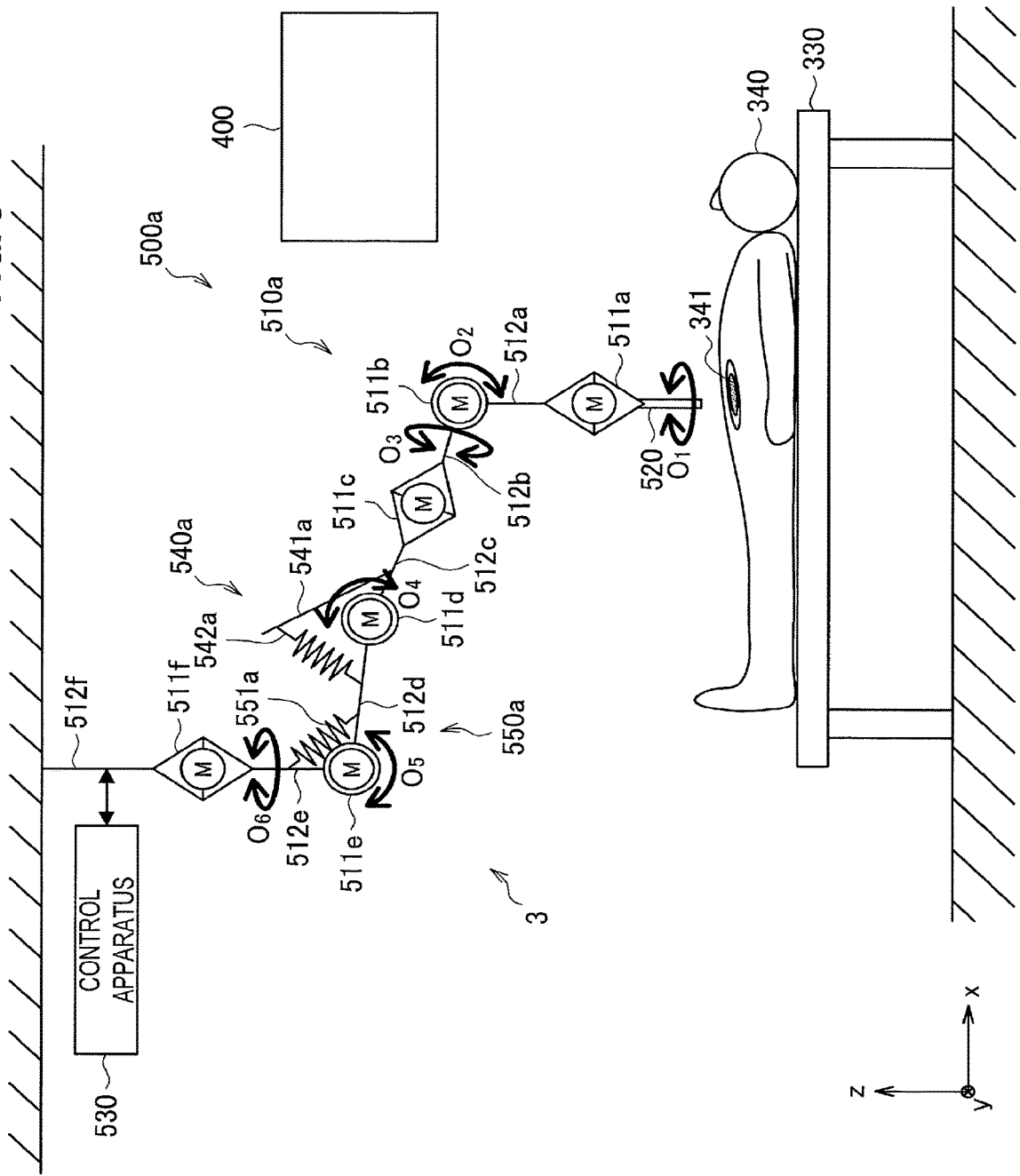
FIG. 8 is a diagram illustrating a schematic configuration of a system and a support arm apparatus according to a modification in which the support arm apparatus is configured as a hanging support arm apparatus.

FIG. 8 will be referenced to describe a modification in which the support arm apparatus is configured as such a hanging support arm apparatus. FIG. 8 is a diagram illustrating a schematic configuration of a system and a support arm apparatus according to a modification in which the support arm apparatus is configured as a hanging support arm apparatus.

FIG. 8 illustrates a situation in which a system 3 according to the present embodiment is used to perform abdominal surgery on a patient 340 on top of an operating table 330. Referring to FIG. 8, the system 3 includes a support arm apparatus 500a and the display apparatus 400. Herein, the system 3 according to the present modification corresponds to modifying the configuration of the arm section 510 of the support arm apparatus 500 in the system 1 described with reference to FIG. 1. Since other configurations and functions in the system 3 are similar to system 1, a description is omitted here.

Referring to FIG. 8, the support arm apparatus 500a according to the present modification includes an arm section 510a, the microscope section 520 attached to the front end of the arm section 510a, and the control apparatus 530 that controls the operation of the support arm apparatus 500a. Since the configurations and functions of the microscope section 520 and the control apparatus 530 are similar to the system 1, a description is omitted here.

As illustrated, the arm section 510a has a base end section attached to the ceiling of the operating room, and is installed to hang down from the ceiling. In this way, the support arm apparatus 500a is what is called a hanging support arm apparatus.

Except for the base end being attached to the ceiling, the arm section 510a has a configuration similar to the arm section 510 of the support arm apparatus 500 illustrated in FIG. 1. In other words, the arm section 510a includes joint sections 511a, 511b, 511c, 511d, 511e, and 511f respectively provided at positions corresponding to each rotation axis (called the first axis $O_1$, the second axis $O_2$, the third axis $O_3$, the fourth axis $O_4$, the fifth axis $O_5$, and the sixth axis $O_6$ in order from the front end side), and multiple links 512a, 512b, 512c, 512d, 512e, and 512f rotatably joined to each other by the joint sections 511b to 511f. Also, on the front end of the arm section 510a, the microscope section 520 is attached via the joint section 511a.

The base end of the link 512f that extends in an approximately vertical direction is attached to the ceiling. The front end of the link 512f is joined to the base end of the link 512e through the joint section 511f, and the link 512f rotatably supports the link 512e through the joint section 511f. Thereafter, similarly, the front ends of the links 512e, 512d, 512c, and 512b are joined to the base ends of the links 512d, 512c, 512b and 512a through the joint sections 511e, 511d, 511c, and 511b, respectively. In addition, the links 512e, 512d, 512c, and 512b rotatably support the links 512d, 512c, 512b, and 512a through the joint sections 511e, 511d, 511c, and 511b, respectively. Furthermore, the microscope section 520 is joined to the front end of the link 512a through the joint section 511a. The link 512a rotatably supports the microscope section 520 through the joint section 511a.

Also, the joint sections 511a to 511f are provided with the actuator 430 illustrated in FIG. 2. By controlling the driving of each actuator 430 in each of the joint sections 511a to 511f by the control apparatus 530, the driving of the arm section 510 is controlled.

Furthermore, similarly to the arm section 510, in the arm section 510a as well, gravity compensation mechanisms 540a and 550a are provided in the joint section 511d corresponding to the fourth axis $O_4$ and the joint section 511e corresponding to the fifth axis $O_5$, respectively.

The gravity compensation mechanism 540a includes a hooking section 541a provided in a fixed manner (that is, rotating together with the link 512c about the joint section 511d) with respect to the link 512c connected to the front end side of the joint section 511d, and a spring 542a stretched in tension between the hooking section 541a and the link 512d connected to the base end side of the joint section 511d. According to such a configuration, by the restoring force of the spring 542a, the gravity compensation mechanism 540a imparts to the joint section 511d a compensating torque in a direction that cancels out the load torque due to the self-weight of the arm section 510a acting on the joint section 511d.

The gravity compensation mechanism 550a includes a spring 551a stretched in tension between the link 512d connected to the front end side of the joint section 511e and the link 512e connected to the base end side of the joint section 511d. According to such a configuration, by the restoring force of the spring 551a, the gravity compensation mechanism 550a imparts to the joint section 511e a compensating torque in a direction that cancels out the load torque due to the self-weight of the arm section 510a acting on the joint section 511e.

In this way, the gravity compensation mechanisms 540a and 550a have functions substantially similar to the gravity compensation mechanisms 540 and 550 in the embodiment described above. In the present modification, similarly to the embodiment described above, gravity compensation in the joint sections 511d and 511e is executed by using both the gravity compensation mechanisms 540a and 550a and the actuators 430 provided in the joint sections 511d and 511e. Consequently, the gravity compensation mechanisms 540a and 550a can be configured more simply, while in addition, it becomes possible to make the actuators 430 provided in the joint sections 511d and 511e more compact.

The above describes the configuration of the system 3 and the support arm apparatus 500a according to a modification in which the support arm apparatus is configured as a hanging support arm apparatus. As described above, the gravity compensation method according to the present embodiment is also applicable to the hanging support arm apparatus 500a, making it possible to obtain advantages similar to the embodiment described above, namely the ability to configure the arm section 510a and the support arm apparatus 500a as a whole in a simpler and more lightweight configuration.

(5-3. Other Modifications)

Besides the above, the present embodiment may also be configured as follows.

For example, in the embodiment described above, the support arm apparatus 500 and 500a are configured as observation apparatus in which the microscope section 520 is provided on the front end of the arm sections 510 and 510a, but the present embodiment is not limited to such an example. For example, the support arm apparatus 500 and 500a may also another type of observation apparatus, in which an observation tool such as an endoscope or an optical microscope section is provided on the front end of the arm sections 510 and 510a. Also, the medical tool provided on the front end of the arm sections 510 and 510a is not limited to an observation tool, and any of various other types of medical tools preferably are attached to the front end of the arm sections 510 and 510a. For example, any of various types of treatment tools, such as forceps, a retractor, a light source for an endoscope or a microscope, or a surgical energy device used to seal blood vessels, for example, may be connected to the front end of the arm sections 510 and 510a.

Also, in the embodiment described above, among the joint sections 511a to 511f of the arm sections 510 and 51a of the support arm apparatus 500 and 500a, the joint section 511d corresponding to the fourth axis $O_4$ and the joint section 511e corresponding to the fifth axis $O_5$ are treated as the targets of gravity compensation, and these joint sections 511d and 511e are provided with the gravity compensation mechanisms 540, 550, 540a, and 550a, but the present embodiment is not limited to such an example. In the present embodiment, only one of either of these joint sections 511d and 511e may be treated as the target of gravity compensation, while the other joint section may not be treated as a target of gravity compensation.

Herein, each of the joint sections 511a to 511f of the arm sections 510 and 510a includes a rotation axis of either a yaw axis or a pitch axis, but for the yaw axes, since the load torque due to the self-weight of the arm sections 510 and 510a is zero because of the rotation axis direction, it is not necessary to perform gravity compensation in the first place. Also, among the pitch axes, for those in which the angle obtained between the horizontal plane and the rotation axis direction changes, since the change in the angle causes the load torque due to the self-weight of the arm sections 510 and 510a as well as the compensating torque by the gravity compensation mechanisms 540, 550, 540a, and 550a to change as well, the design of the gravity compensation mechanisms 540, 550, 540a, and 550a becomes difficult. Furthermore, even with a pitch axis, in the case in which the rotation axis direction is largely divergent from a state of being parallel with the horizontal plane (for example, in the extreme case of the rotation axis direction being orthogonal to the horizontal plane), since the load torque due to the self-weight of the arm sections 510 and 510a becomes smaller (becoming zero in the case in which the rotation axis direction and the horizontal plane are orthogonal), it is not necessary to perform gravity compensation in the first place. Consequently, in the present embodiment, the joint sections to treat as the targets of gravity compensation (also called the compensated joint sections for the sake of convenience) favorably may be those among the pitch axes in which the angle obtained between the plane orthogonal to the vertical direction (that is, the horizontal plane) and the rotation axis direction is constant. Furthermore, if the significance of performing gravity compensation is considered, it is particularly preferable for a joint section whose rotation axis is parallel to the horizontal plane and most susceptible to the influence of the load torque to be a compensated joint section.

If the arrangement of yaw axes and pitch axes in the arm sections 510 and 510a is considered, for the pitch axes, in the case in which a yaw axis whose rotation axis is not parallel to the vertical direction is provided on the base end side, the angle obtained between the horizontal plane and the rotation axis direction of the pitch axis changes according to the rotation about the yaw axis. Consequently, among the pitch axes, the ones in which the angle between the horizontal plane and the rotation axis direction is constant may be positioned on the base end side of the arm sections 510 and 510a. On the other hand, typically, in an arm section having six rotation axes, like the arm sections 510 and 510a illustrated in FIGS. 1 and 7, the rotation axes are disposed from the base end side in the order of a yaw axis (sixth axis $O_6$), a pitch axis (fifth axis $O_5$), a pitch axis (fourth axis $O_4$), a yaw axis (third axis $O_3$), a pitch axis (second axis $O_2$), and a yaw axis (first axis $O_1$), while in addition, the yaw axis (sixth axis $O_6$) farthest on the base end side is disposed to have the rotation axis parallel to the vertical direction in many cases. In the arm sections 510 and 510a having such a configuration, the pitch axes (fifth axis $O_5$ and fourth axis $O_4$) disposed between the yaw axis (sixth axis $O_6$) provided farthest on the base end side and the next provided yaw axis (third axis $O_3$) may become pitch axes in which the rotation axis direction constantly stays parallel to the horizontal plane. Consequently, if a typical configuration of the arm section is anticipated, adopting the joint sections corresponding to the pitch axes provided on the base end side as the compensated joint sections may be considered preferable.

Note that in the case of the exemplary configurations illustrated in FIGS. 1 and 7, as above, the fourth axis $O_4$ and the fifth axis $O_5$ are pitch axes in which the rotation axis constantly stays parallel to the horizontal plane. Consequently, in the embodiment described above, as the joint sections favorable for performing gravity compensation, a case is described in which the joint sections 511d and 511e corresponding to the fourth axis $O_4$ and the fifth axis $O_5$ are the compensated joint sections.

Also, in the embodiment described above, actuators 430 are provided in all of the joint sections 511a to 511f of the arm sections 510 and 510a of the support arm apparatus 500 and 500a, but the present embodiment is not limited to such an example. In the present embodiment, among the joint sections 511a to 511f, it is sufficient to provide the actuator 430 in at least one joint section acting as a compensated joint section. In other words, in the present embodiment, it is sufficient to provide the gravity compensation mechanisms 540, 550, 540a, and 550a as well as the actuators 430 in the joint sections acting as the compensated joint sections, while the other joint sections may have any configuration. Note that in this case, since the whole body cooperative control described above may not be executed, the control of the operation of the arm section configured in this way, that is, the driving control of the joint sections provided with the actuators 430, preferably is executed by any of various known methods. However, at this state, the method of controlling the driving the actuators 430 related to gravity compensation may be performed similarly to the embodiment described above. In other words, the actuators 430 may be driven by taking into account the compensating torque by the gravity compensation mechanisms 540, 550, 540a, and 550a to produce a generated torque that may cancel out the load torque due to the self-weight of the arm section.

In this way, in the present embodiment, the actuator 430 may be either present or absent in each joint section not subjected to gravity compensation, and correspondingly, the arm section control method (that is, the actuator control method) may also be any method. In other words, the control method of the arm section according to the present embodiment is not limited to one that uses the whole body cooperative control and the ideal joint control described above, and the control of the arm section preferably is executed using any of various known types of methods. Regardless of the control method, by driving the actuators 430 to take into account the compensating torque by the gravity compensation mechanisms 540, 550, 540a, and 550a to produce a generated torque that may cancel out the load torque due to the self-weight of the arm section, the gravity compensation according to the present embodiment may be realized.

6. COMPARISON WITH TYPICAL GRAVITY COMPENSATION

At this point, gravity compensation according to the present embodiment and typical existing gravity compensation will be compared as mathematical formulas. Herein, as one example of typical gravity compensation, gravity compensation using the support arm apparatus described in Patent Literature 3 submitted previously by the applicant will be examined.

In the support arm apparatus described in Patent Literature 3, actuators are provided in all of the joint sections included in the arm section, and similarly to the present embodiment, the operation of the arm section is controlled by whole body cooperative control and ideal joint control. In the case of performing gravity in this support arm apparatus, control that supports the self-weight of the arm section may be executed by driving the actuators. If one attempts to compensate the load torque due to the self-weight of the arm section with the generated torque $\tau_a$ of the actuators, the generated torque $\tau_a$ computed in whole body cooperative control may be expressed as in Formula (15) below. Also, a formula indicating the motion of the actuators in ideal joint control at this point may be expressed as in Formula (16) below (note that Formula (16) below is the same as Formula (12) above).

[Math. 14]

$$\tau_a = M(q)\ddot{q} + V(q,\dot{q}) + G(q) \tag{15}$$

$$I_a \ddot{q}^{ref} = \tau_a + \tau_e - \nu_a \dot{q} \tag{16}$$

Herein, q is the rotational angle in a joint section. Also, in Formula (15) above, the first right-hand side term (M(q)q″) is a term expressing inertial force, the second right-hand side term (V(q, q′)) is a term expressing centrifugal force and the Coriolis force, and the third right-hand side term (G(q)) is a term expressing the load torque due to the self-weight of the arm section. From Formula (15) above, in the support arm apparatus described in Patent Literature 3, for gravity compensation, there occurs a need to produce enough torque to cancel out the load torque G(q) as the generated torque $\tau_a$. Consequently, a large output from the actuators becomes necessary, and the actuators become bulkier. As a result, the arm section and the support arm apparatus as a whole become bulkier and heavier.

In contrast, in the present embodiment, gravity compensation may be performed by using both the gravity compensation mechanisms 540, 550, 540a, and 550a as well as the actuators 430. At this time, the driving control of the actuators 430 is executed by mathematical operations for gravity compensation in the whole body cooperative control for the functional configuration illustrated in FIG. 4, or in the ideal joint control for the functional configuration illustrated in FIG. 7.

As in the functional configuration illustrated in FIG. 4, in the case in which the mathematical operations for gravity compensation are performed in the whole body cooperative control, the generated torque $\tau_a$ computed in the whole body cooperative control may be expressed as in Formula (17) below. Also, a formula indicating the motion of the actuators in ideal joint control at this point may be expressed as in Formula (18) below (note that Formula (18) below is the same as Formulas (12) and (16) above).

[Math. 15]

$$\tau_a = M(q)\ddot{q} + V(q,\dot{q}) + G(q) - G_s(q) \tag{17}$$

$$I_a \ddot{q}^{ref} = \tau_a + \tau_e - \nu_a \dot{q} \tag{18}$$

Here, $G_s$ is the compensating torque by the gravity compensation mechanisms 540, 550, 540a, and 550a. As illustrated in Formula (18) above, in the present embodiment, for gravity compensation, it is sufficient to generate a torque corresponding to $G(q)-G_s(q)$ as the generated torque $\tau_a$. Consequently, compared to the support arm apparatus described in Patent Literature 3, since the output demanded of the actuators 430 becomes smaller, it becomes possible to make the actuators 430 more compact. Also, in the present embodiment, the gravity compensation mechanisms 540, 550, 540a, and 550a are configured such that $G(q)-G_s(q) \neq 0$ and $G(q)-G_s(q) > 0$. In other words, it is not necessary to nearly completely cancel out the load torque $G(q)$ due to the self-weight of the arm sections 510 and 510a with the compensating torque by the gravity compensation mechanisms 540, 550, 540a, and 550a. Consequently, since the gravity compensation mechanisms 540, 550, 540a, and 550a can take a simple configuration, it becomes possible to minimize increases in the bulk of the arm sections 510 and 510a due to providing the gravity compensation mechanisms 540, 550, 540a, and 550a.

On the other hand, as in the functional configuration illustrated in FIG. 7, in the case in which the mathematical operations for gravity compensation are performed in the ideal joint control, the generated torque $\tau_a$ computed in the whole body cooperative control may be expressed as in Formula (19) below (note that Formula (19) below is the same as Formula (15) above). Also, a formula indicating the motion of the actuators in ideal joint control at this point may be expressed as in Formula (20) below.

[Math. 16]

$$\tau_a = M(q)\ddot{q} + V(q,\dot{q}) + G(q) \tag{19}$$

$$I_a \ddot{q}^{ref} = \tau_a + \tau_e - \nu_a \dot{q} - G_s(q) \tag{20}$$

In such a case, as illustrated in Formula (19) above, a relatively large value to cancel out the load torque G(q) may be computed as the generated torque $\tau_a$ computed in the whole body cooperative control, similarly to the support arm apparatus described in Patent Literature 3. However, as illustrated in Formula (20) above, in the later mathematical operations in the ideal joint control, by taking the compensating torque $G_s(q)$ into account, a smaller value obtained by subtracting the compensating torque $G_s(q)$ component is computed as the torque command value ultimately given to the actuators 430. Consequently, similarly to the functional configuration illustrated in FIG. 4, in this functional configuration, the output of the actuators 430 can be reduced further compared to the support arm apparatus described in Patent Literature 3, and it becomes possible to make the actuators 430 more compact. Also, similarly, since the gravity compensation mechanisms 540, 550, 540a, and 550a are configured such that $G(q)-G_s(q)>0$, the gravity compensation mechanisms 540, 550, 540a, and 550a can take a simple configuration, and it becomes possible to make the arm sections 510 and 510a more compact.

7. SUPPLEMENT

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

For example, the target of application of the technology according to the present disclosure is not limited to the medical field, and may also be fields other than the medical field. For example, the technology according to the present disclosure is also favorably applicable to gravity compensation in an industrial support arm apparatus used for product assembly and inspection steps in a factory. By using the technology according to the present disclosure, in an industrial support arm apparatus, similarly to the embodiment described above, it is possible to configure the support arm apparatus in a more compact and lightweight configuration, and advantageous effects such as reduced manufacturing costs and an improved degree of freedom in the installation space can be obtained.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

A medical support arm apparatus including:

an arm section including multiple joint sections, and configured such that a medical tool is provided on a front end;

an actuator provided at least in a compensated joint section that is a target of gravity compensation among the joint sections, and including a torque sensor that detects a torque acting on the compensated joint section; and a gravity compensation mechanism that imparts to the compensated joint section a compensating torque in a direction that cancels out a load torque due to a self-weight of the arm section acting on the compensated joint section.

(2)

The medical support arm apparatus according to (1), in which the gravity compensation mechanism includes a spring that generates the compensating torque, and the spring is provided to extend and contract monotonically in association with a rotation of the compensated joint section.

(3)

The medical support arm apparatus according to (1) or (2), further including:

a control apparatus that at least controls a driving of the compensated joint section by causing the actuator to operate on the basis of at least a state of the compensated joint section detected by the torque sensor, in which the control apparatus performs gravity compensation by taking the compensating torque into account to cause the actuator to operate to generate a torque that works to cancel out the load torque.

(4)

The medical support arm apparatus according to (3), in which the control apparatus computes a generated torque in the joint sections as a control value for a whole body cooperative control of the arm section by generalized inverse dynamics using a state of the arm section acquired on the basis of multiple states of the joint sections provided with the actuator, a purpose of motion of the arm section, and a constraint condition, and causes the actuator to operate on the basis of the computed generated torque.

(5)

The medical support arm apparatus according to (4), in which the control value is computed on the basis of a virtual force, which is an imaginary force acting to achieve the purpose of motion in an operation space describing a relationship between a force acting on the arm section and an acceleration produced in the arm section, and an actual force computed by converting the virtual force into a real force for driving the joint sections on the basis of the constraint condition.

(6)

The medical support arm apparatus according to (4) or (5), in which when computing the generated torque with respect to the compensated joint section in the whole body cooperative control, the control apparatus computes the compensating torque expressed as a function of a rotational angle of the compensated joint section, and computes a difference between the computed compensating torque and the load torque acting on the compensated joint section by the self-weight of the arm section as a gravity compensation component included in the generated torque.

(7)

The medical support arm apparatus according to any one of (4) to (6), in which the control apparatus computes a generated torque in the joint sections as a command value that achieves an ideal response of the arm section by correcting an influence of a disturbance with respect to the control value, and causes the actuator to operate on the basis of the computed generated torque.

(8)

The medical support arm apparatus according to (7), in which the command value is computed by correcting the control value using a disturbance estimation value expressing an influence of a disturbance with respect to a driving of the joint sections estimated on the basis of detected states of the joint sections.

(9)

The medical support arm apparatus according to (4) or (5), in which the control apparatus computes a generated torque in the joint sections as a command value that achieves an ideal response of the arm section by correcting an influence of a disturbance with respect to the control value, and causes the actuator to operate on the basis of the computed generated torque, and when computing the generated torque according to the command value with respect to the compensated joint section, the control apparatus computes the generated torque according to the command value by computing the compensating torque expressed as a function of a rotational angle of the compensated joint section, treating a value obtained by subtracting the compensating torque computed from the generated torque computed as a control value for the whole body cooperative control as a generated torque according to the control value, and correcting the influence of the disturbance.

(10)

The medical support arm apparatus according to any one of (1) to (9), in which the compensated joint section is one or two of the joint sections provided farther on a base end side of the arm section and including a rotation axis corresponding to a pitch axis.

(11)

The medical support arm apparatus according to any one of (1) to (10), in which the medical tool is an observation tool for observing a surgical site of a patient.

(12)

A medical system including:

a medical support arm apparatus including an arm section including multiple joint sections, and configured such that an observation tool for observing a surgical site of a patient is provided on a front end, an actuator provided in at least one of the joint sections and including a torque sensor that detects a torque acting on the joint section, and a gravity compensation mechanism that imparts, to each joint section provided with the actuator, a compensating torque that compensates a load torque caused by a self-weight of the arm section acting on the joint section, and a control apparatus that causes the actuator to operate on the basis of at least a state of the joint section detected by the torque sensor, and controls a driving of the joint section; and a display apparatus that displays an image captured by the observation tool of the medical support arm apparatus.

(13)

A surgical microscope system including:

an arm section including multiple joint sections that include actuators;

a microscope for imaging a surgical site of a patient, provided on a front end of the arm section such that an imaging direction is changeable by controlling the actuators;

a gravity compensation mechanism that imparts to a compensated joint section, which is a target of gravity compensation among the joint sections, a compensating torque in a direction that cancels out a load torque due to a self-weight of the arm section acting on the compensated joint section; and a display apparatus that displays an image captured by the microscope.

(14)

The surgical microscope system according to (13), in which the gravity compensation mechanism includes a spring that generates the compensating torque, and the spring is provided to extend and contract in association with a rotation of the compensated joint section.

(15)

The surgical microscope system according to (13), in which the microscope is provided with a multi-chip imaging section.

(16)

The surgical microscope system according to (13), in which the display apparatus is configured to present a 3D display on the basis of images captured by the microscope.

REFERENCE SIGNS LIST 1, 2, 3 system
10, 10a, 500, 500a support arm apparatus
20, 20a, 530 control apparatus
30, 400 display apparatus
120, 510, 510a arm section
130, 511a, 511b, 511c, 511d, 511e, 511f joint section
131 joint driving section
132 rotational angle detection section
133 torque detection section
140 gravity compensation mechanism section
150, 520 microscope section
220 storage section
240, 240a whole body cooperative control section
241 arm state acquisition section
242 operation condition setting section
243 virtual force computing section
244, 244a actual force computing section
245, 253 compensating torque computing section
250, 250a ideal joint control section
251 disturbance estimation section
252, 252a command value computing section
260 driving control section
430 actuator
424, 611 motor
425 motor driver
426, 612 reduction gear
427, 613 encoder
428, 614 torque sensor
512a, 512b, 512c, 512d, 512e, 512f link
540, 540a, 550, 550a gravity compensation mechanism
541, 541a, 551 hooking section
542, 542a, 551a, 552 spring

The invention claimed is:

1. A medical support arm apparatus comprising:
an arm section including multiple joint sections, and configured to have a medical tool attached to a front end thereof;
an actuator provided at least in a compensated joint section that is a target of gravity compensation among the multiple joint sections, and including a torque sensor that detects a torque acting on at least the compensated joint section;
a gravity compensation mechanism that includes a spring that imparts to the compensated joint section a compensating torque in a direction that cancels out a load torque due to a self-weight of the arm section acting on the compensated joint section; and control circuitry that at least controls a driving of the compensated joint section by causing the actuator to operate on a basis of at least a state of the compensated joint section detected by the torque sensor, wherein the control circuitry controls gravity compensation by taking the compensating torque into account to cause the actuator to generate a torque that counteracts the load torque, and the control circuitry is configured to compute a generated torque for respective of the multiple of joints as a control value for a whole body cooperative control of the arm section by generalized inverse dynamics using a state of the arm section acquired on a basis of multiple states of the multiple joint sections provided with the actuator, a task performed by the arm section, and a constraint condition, and causes the actuator to operate on a basis of the computed generated torque.

2. The medical support arm apparatus according to claim 1, wherein the gravity compensation mechanism includes the spring that generates the compensating torque, and the spring is provided to extend and contract monotonically in association with a rotation of the compensated joint section.

3. The medical support arm apparatus according to claim 1, wherein the control value is computed by the control circuitry on a basis of a virtual force, which is an imaginary force acting to achieve the task performed by the arm section in an operation space describing a relationship between a force acting on the arm section and an acceleration produced in the arm section, and an actual force computed by converting the virtual force into a real force for driving the multiple joint sections on a basis of the constraint condition.

4. The medical support arm apparatus according to claim 1, wherein when computing a generated torque with respect to the compensated joint section in the whole body cooperative control, the control circuitry computes the compensating torque expressed as a function of a rotational angle of the compensated joint section, and computes a difference between the computed compensating torque and the load torque acting on the compensated joint section by the self-weight of the arm section as a gravity compensation component included in the generated torque.

5. The medical support arm apparatus according to claim 1, wherein the control circuitry is configured to compute the generated torque at least in the compensated joint section as a command value that achieves an ideal response of the arm section by correcting an influence of a disturbance with respect to the control value, and causes the actuator to operate on a basis of the computed generated torque for the compensated joint section and the at least another joint section.

6. The medical support arm apparatus according to claim 5, wherein the command value is computed by correcting the control value using a disturbance estimation value expressing an influence of a disturbance with respect to a driving of the joint sections estimated on a basis of detected states of the joint sections.

7. The medical support arm apparatus according to claim 1, wherein the control circuitry is configured to compute the generated torque in at least the compensated joint, section as a command value that achieves an ideal response of the arm section by correcting an influence of a disturbance with respect to the control value, and causes the actuator to operate on a basis of the computed generated torque, and when computing the generated torque according to the command value with respect to the compensated joint section, the control circuitry computes the generated torque according to the command value by computing the compensating torque expressed as a function of a rotational angle of the compensated joint section, treating a value obtained by subtracting the compensating torque computed from the generated torque computed as a control value for the whole body cooperative control as a generated torque according to the control value, and correcting the influence of the disturbance.

8. The medical support arm apparatus according to claim 1, wherein the compensated joint section is one or two of the joint sections provided farther on a base end side of the arm section and including a rotation axis corresponding to a pitch axis.

9. The medical support arm apparatus according to claim 1, wherein the medical tool is an observation tool for observing a surgical site of a patient.

10. A medical system comprising:

a medical support arm apparatus including an arm section including multiple joint sections, and configured such that an observation tool for observing a surgical site of a patient is provided on a front end, an actuator provided in at least one of the multiple joint sections and including a torque sensor that detects a torque acting on the at least one joint section, and a gravity compensation mechanism that includes a spring that imparts, to each joint section provided with the actuator, a compensating torque that compensates a load torque caused by a self-weight of the arm section acting on each joint section provided with the actuator, and control circuitry that is configured to control the actuator to operate on a basis of at least a state of the at least one joint section detected by the torque sensor, and controls a driving of the at least one joint section; and a display apparatus that displays an image captured by the observation tool of the medical support arm apparatus, wherein the control circuitry is configured to control gravity compensation by taking the compensating torque into account to cause the actuator to counteract the load torque, and the control circuitry is also configured to compute a generated torque as a control value for a whole body cooperative control of the arm section by generalized inverse dynamics using a state of the arm section acquired on a basis of multiple states of the at least one joint section provided with the actuator, a task performed by the arm section, and a constraint condition, and causes the actuator to operate on a basis of the computed generated torque for the at least one joint section provided with an actuator.

11. A surgical microscope system comprising:
an arm section including multiple joint sections that include actuators;
a microscope for imaging a surgical site of a patient, provided on a front end of the arm section such that an imaging direction is changeable by controlling the actuators;
a gravity compensation mechanism that includes a spring that imparts to a compensated joint section, which is a target of gravity compensation among the multiple joint sections, a compensating torque in a direction that cancels out a load torque due to a self-weight of the arm section acting on the compensated joint section;
a display apparatus that displays an image captured by the microscope; and
control circuitry that at least controls a driving of the compensated joint section by causing the actuators to operate on a basis of at least a state of the compensated joint section detected by the torque sensor, wherein
the control circuitry performs gravity compensation by taking the compensating torque into account to cause the actuators to generate a torque that counteracts the load torque for each of the multiple joint sections that include actuators, and
the control circuitry is configured to compute a generated torque as a control value for a whole body cooperative control of the arm section by generalized inverse dynamics using a state of the arm section acquired on a basis of multiple states of the multiple joint sections, a task performed by the arm section, and a constraint condition, and causes the actuators to operate on a basis of the computed generated torque.

12. The surgical microscope system according to claim 11, wherein
the gravity compensation mechanism includes the spring that generates the compensating torque, and
the spring is provided to extend and contract in association with a rotation of the compensated joint section.

13. The surgical microscope system according to claim 11, wherein
the microscope is provided with a multi-chip imaging section.

14. The surgical microscope system according to claim 11, wherein
the display apparatus is configured to present a 3D display on a basis of images captured by the microscope.

* * * * *